United States Patent
Peh et al.

(10) Patent No.: US 9,937,296 B2
(45) Date of Patent: Apr. 10, 2018

(54) VASCULAR ACCESS DEVICE AND GUIDING PORTION

(71) Applicant: Agency for Science, Technology and Research, Singapore (SG)

(72) Inventors: Ruey Feng Peh, Singapore (SG); Jing Ming Chew, Singapore (SG); Wei Ling Fiona Loke, Singapore (SG); Hsien Ts'ung Tay, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 188 days.

(21) Appl. No.: 14/417,314

(22) PCT Filed: Jul. 26, 2013

(86) PCT No.: PCT/SG2013/000311
§ 371 (c)(1),
(2) Date: Jan. 26, 2015

(87) PCT Pub. No.: WO2014/017986
PCT Pub. Date: Jan. 30, 2014

(65) Prior Publication Data
US 2015/0190587 A1    Jul. 9, 2015

(30) Foreign Application Priority Data
Jul. 26, 2012   (SG) .................................. 201205574

(51) Int. Cl.
*A61M 5/32* (2006.01)
*A61M 5/158* (2006.01)
(Continued)

(52) U.S. Cl.
CPC ....... *A61M 5/3273* (2013.01); *A61B 17/0057* (2013.01); *A61B 18/1477* (2013.01);
(Continued)

(58) Field of Classification Search
CPC ...... A61M 39/0208; A61M 2039/0223; A61M 2039/0232; A61M 2039/0235;
(Continued)

(56) References Cited

U.S. PATENT DOCUMENTS 2,828,744 A   4/1958  Hirsch et al.
3,094,122 A   6/1963  Gauthier et al.
(Continued)

FOREIGN PATENT DOCUMENTS

CN   1213319 A   4/1999
EP   0356810 A2   3/1990
(Continued)

OTHER PUBLICATIONS

Extended European Search Report dated Oct. 6, 2016 from European Patent Application No. 13823444.8.
(Continued)

*Primary Examiner* — Kami A Bosworth
*Assistant Examiner* — William Carpenter
(74) *Attorney, Agent, or Firm* — K. David Crockett, Esq.; Niky Economy Syrengelas, Esq.; Crockett & Crockett, PC

(57) ABSTRACT

According to various embodiments, a method and system to obtain access to a blood vessel underneath a skin layer that may preserve lifespan of the blood vessel and reduce executional skill variability may be provided. The method includes placing a guiding portion between the blood vessel and the skin layer; and configuring the guiding portion to receive and guide a needle to reach the same location of the blood vessel repeatedly and consistently; and forming a resultant scarred track between the blood vessel and the skin layer as the guiding portion is resorbed over time. The system includes a vascular access device configurable to first possess strength to penetrate through a tissue layer, subsequently possess flexibility to conform to the surrounding
(Continued)

tissue beneath the tissue layer; and a guiding portion which may be resorbable, wherein the inlet includes a larger diameter compared to the outlet.

20 Claims, 37 Drawing Sheets

(51) Int. Cl.
| | |
|---|---|
| *A61M 1/36* | (2006.01) |
| *A61B 17/00* | (2006.01) |
| *A61B 18/14* | (2006.01) |
| *A61B 90/80* | (2016.01) |
| *A61M 39/02* | (2006.01) |
| *A61B 17/06* | (2006.01) |
| *A61B 17/132* | (2006.01) |
| *A61B 18/00* | (2006.01) |
| *A61B 90/00* | (2016.01) |

(52) U.S. Cl.
CPC .............. *A61B 90/39* (2016.02); *A61B 90/80* (2016.02); *A61M 1/3653* (2013.01); *A61M 1/3659* (2014.02); *A61M 5/158* (2013.01); *A61M 5/329* (2013.01); *A61M 5/3286* (2013.01); *A61M 5/3287* (2013.01); *A61M 39/0208* (2013.01); *A61M 39/0247* (2013.01); *A61B 17/06114* (2013.01); *A61B 17/132* (2013.01); *A61B 2017/00004* (2013.01); *A61B 2017/00526* (2013.01); *A61B 2017/00557* (2013.01); *A61B 2017/00867* (2013.01); *A61B 2018/00577* (2013.01); *A61B 2090/062* (2016.02); *A61B 2090/3962* (2016.02); *F04C 2270/0421* (2013.01)

(58) Field of Classification Search
CPC .. A61M 2039/0238; A61M 2039/0244; A61M 1/3653; A61M 1/3655; A61M 1/3659; A61M 1/3661; A61M 39/0247; A61M 2039/0258; A61M 2039/0261; A61M 2039/027; A61B 17/0057; A61B 2017/00641; A61B 17/3423; A61B 17/11; A61B 2017/1107
See application file for complete search history.

(56) References Cited

U.S. PATENT DOCUMENTS

| | | | | |
|---|---|---|---|---|
| 3,782,381 | A | * | 1/1974 | Winnie .............. A61B 17/3401 604/164.09 |
| 4,013,080 | A | * | 3/1977 | Froning ............. A61B 17/3401 604/165.01 |
| 4,183,357 | A | | 1/1980 | Benson et al. |
| 4,318,401 | A | * | 3/1982 | Zimmerman ...... A61B 17/3415 604/165.01 |
| RE31,855 | E | | 3/1985 | Osborne |
| 4,822,341 | A | * | 4/1989 | Colone .............. A61M 1/3655 604/175 |
| 4,846,799 | A | * | 7/1989 | Tanaka .................... A61M 5/32 604/158 |
| 4,846,812 | A | | 7/1989 | Walker et al. |
| 4,878,904 | A | * | 11/1989 | Callaway ................ A61M 5/34 604/272 |
| 4,906,236 | A | | 3/1990 | Alberts et al. |
| 4,973,317 | A | | 11/1990 | Bobrove |
| 5,232,442 | A | * | 8/1993 | Johnson ............ A61M 25/0102 604/158 |
| 5,441,489 | A | | 8/1995 | Utsumi et al. |
| 5,630,833 | A | | 5/1997 | Katsaros et al. |
| 5,910,133 | A | * | 6/1999 | Gould ............ A61B 17/320725 604/164.03 |
| 6,007,576 | A | * | 12/1999 | McClellan .............. A61F 2/064 623/23.64 |
| 6,019,788 | A | * | 2/2000 | Butters ................ A61B 17/064 604/8 |
| 6,626,863 | B1 | | 9/2003 | Berler |
| 6,695,860 | B1 | | 2/2004 | Ward et al. |
| 6,733,515 | B1 | * | 5/2004 | Edwards .......... A61B 17/00491 604/264 |
| 8,277,437 | B2 | * | 10/2012 | Saal .................... A61B 17/3401 604/508 |
| 8,690,816 | B2 | * | 4/2014 | Dakin .................... A61B 17/11 604/264 |
| 8,747,359 | B2 | * | 6/2014 | Pakter ................ A61B 17/3417 604/164.01 |
| 9,119,906 | B2 | | 9/2015 | Tomantschger et al. |
| 2002/0077658 | A1 | | 6/2002 | Ginn |
| 2004/0102804 | A1 | | 5/2004 | Chin |
| 2008/0195124 | A1 | * | 8/2008 | Borghi ................... A61B 17/11 606/153 |
| 2009/0131919 | A1 | | 5/2009 | Davey |
| 2009/0209918 | A1 | * | 8/2009 | Berglund ............ A61M 1/3655 604/175 |
| 2009/0270835 | A1 | | 10/2009 | Kushner |
| 2010/0191166 | A1 | | 7/2010 | Phillips et al. |
| 2010/0274223 | A1 | | 10/2010 | Teitelbaum et al. |
| 2010/0318016 | A1 | * | 12/2010 | Nugent ............... A61L 27/3808 604/8 |
| 2011/0213309 | A1 | * | 9/2011 | Young ................ A61B 17/0057 604/175 |
| 2012/0101525 | A1 | | 4/2012 | Jenson et al. |

FOREIGN PATENT DOCUMENTS

| | | |
|---|---|---|
| GB | 2282760 A | 4/1995 |
| JP | 11500031 | 1/1999 |
| JP | 2005349121 | 12/2005 |
| WO | WO9535126 A1 | 12/1995 |
| WO | WO2006045608 | 5/2006 |
| WO | WO2010011995 | 1/2010 |
| WO | WO2010011995 A1 | 1/2010 |
| WO | WO2010088532 A1 | 8/2010 |
| WO | WO2010107698 A2 | 9/2010 |
| WO | WO2013128292 A2 | 9/2013 |
| WO | WO2015089372 A1 | 6/2015 |

OTHER PUBLICATIONS

Seldinger, Catheter Replacement of the Needle in Percutaneous Arteriography, 39 Acta Radiologica 368 (May 1, 1953), http://dx.doi.org/10.3109/00016925309136722.
Stuart, Renal Devices: New Blood Revitalizes Dialysis Industry, 18 Start Up (2011).
Loon, et al., Buttonhole Needling of Haemodialysis Arteriovenous Fistulae Results in Less Complications and Interventions Compared to the Rope-Ladder Technique, 25 Nephrol Dial Transplant 225 (2010).
Supplementary Partial European Search Report dated Mar. 17, 2016 from European Patent Application No. 13823444.8.
Office Action dated Sep. 26, 2016 from Chinese Patent Application No. 201380050495.2.
Office Action dated Mar. 27, 2017 from Japanese Patent Application No. 2015-524228.

\* cited by examiner

VASCULAR ACCESS DEVICE AND GUIDING PORTION

CROSS-REFERENCE TO RELATED APPLICATION

The present application is the National Stage Entry of PCT/SG2013/000311 filed on 26 Jul. 2013 and claims the benefit of Singapore patent application no. 201205574-5 filed on 26 Jul. 2012, the entire contents of which are incorporated herein by reference for all purposes.

TECHNICAL FIELD

The present invention relates to a device and a system for vascular access, for example, a device and a system for vascular access for hemodialysis. The present invention also relates to a guiding portion for use in vascular access.

BACKGROUND

A patient with end-stage renal disease would be required to undergo hemodialysis as often as three times a week for up to four hours each time. Hemodialysis is a procedure to clean the patient's blood and remove extra fluid in the form of urine, a process carried out by our kidneys. Hemodialysis requires vascular access to the patient whereby needles are penetrated into the patient body so as to establish blood flow between the patient and a dialysis machine to carry out hemodialysis.

Hemodialysis may be performed in the hospital, a dialysis centre or at home. In the hospital and dialysis centre, vascular access is performed by trained medical professionals, such as nurses or doctors. Generally, in the hospital and dialysis centre setting, medical professionals rotate the cannulation of the blood vessel, most commonly an arteriovenous fistula, between 5-7 sites that are spaced 2-3 cm apart to distribute the trauma experienced by the arteriovenous fistula from repeated needling evenly across the vessel. This is known as "rope ladder" technique. However, this technique is not ideal as patients generally do not have that long an arteriovenous fistula to accommodate 5-7 rotation sites and the rotation sequence may not be followed strictly due to workflow challenges, leading to complications such as aneurysms, stenosis and thrombosis. In fact, as much as one third of dialysis cost goes towards managing vascular access and complications each year (Source: Mary Stuart, Startup 2011). The "buttonhole" technique is an alternative needling technique where cannulation of the arteriovenous fistula is performed consistently at the same location of the vessel wall, and via the same punctured track between the vessel and the skin. This technique has been shown to minimize pain and to disrupt the biological mechanism that causes stenosis known as neo intimal hyperplasia. The buttonhole technique has also been shown to extend arteriovenous fistula lifespan and reduce complication rate in clinical studies (Source: M. M van Loon et al., 2009). Despite its advantages, the buttonhole technique is only available for limited number of patients as this technique is difficult to execute and is usually performed blind relying heavily on experience and skill. Further, before a patient can adopt buttonhole cannulation, a scarred tracked between the arteriovenous fistula and the skin needs to be created by blind and repeated needling through the exact trajectory across the subcutaneous tissue between the skin and the arteriovenous fistula, by the same medical professional over 10-20 dialysis sessions. This further heightens the barrier and the skills for buttonhole technique to be widely adopted.

In the home environment as well, the patient or his or her family member usually lacks the experience and skill to carry the needling technique without which the risk of trauma to the patient's blood vessel would be increased due to repeated needle punctures from unsuccessful vascular access. This often compromises the safety of the patient during dialysis, lowers the lifespan of a healthy arteriovenous fistula and increase costs of the hemodialysis treatments required to treat resulting vascular access complications. The lack of medical expertise or vascular access skills at home is also a decisive hurdle for home hemodialysis technologies from being adopted.

As such, there is a need for a device and a system to lower the skill variability in administrating of needles into the patient's arteriovenous fistula using the buttonhole technique by either the medical professional or the patient himself. An invention that can achieve that would help prolong the lifespan of the arteriovenous fistula, alleviate the risk of the patient, and reduce cost of hemodialysis treatments that goes to repairing and/or treating vascular access complications resulted by needling.

SUMMARY

In various embodiments, a vascular access device may be provided. The vascular access device may include a needle having a tip portion; and a shield arranged around and at least substantially along a longitudinal axis of the needle, wherein the shield is substantially rigid so as to provide strength to the tip portion to penetrate a tissue layer as the tip portion extends out from the shield and the needle gradually conforms to the surrounding tissue beneath the tissue layer as the distance between the tip portion and the shield increases.

In various embodiments, a guiding portion may be provided. The guiding portion may be configured to be placed above a blood vessel and configured to receive and guide a needle to reach the same location of the blood vessel repeatedly and consistently. The guiding portion may include a channel portion including an inlet and an outlet; wherein the channel portion is configured to be resorbed over time.

In various embodiments, a vascular access system may be provided. The vascular access system may include a vascular access device and a guiding portion.

In various embodiments, a method to obtain access to a blood vessel underneath a skin layer may be provided. The method may include placing a guiding portion between the blood vessel and the skin layer; and configuring the guiding portion to receive and guide a needle to reach the same location of the blood vessel repeatedly and consistently.

In various embodiments, a method to create vascular access track underneath a skin layer may be provided. The method may include placing a guiding portion between the blood vessel and the skin layer; configuring the guiding portion to receive and guide a needle; and forming a resultant scarred track between the blood vessel and the skin layer as the guiding portion is resorbed over time.

In various embodiments, a method to obtain access to a blood vessel underneath a skin layer may be provided. The method may include inserting a tissue scarring device through the skin layer to reach the blood vessel; and forming a resultant scarred track between the blood vessel and the skin layer as the tissue scarring device is retracted.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DESCRIPTION

Embodiments described below in context of the devices and systems are analogously valid for the respective methods, and vice versa. Furthermore, it will be understood that the embodiments described below may be combined, for example, a part of one embodiment may be combined with a part of another embodiment.

FIGS. 1A to 1G illustrate a vascular access device 102 which is able to penetrate through a tissue layer (shown later in FIGS. 2A to 2C) but automatically losses column strength after piercing through the tissue layer, and gradually conforms to its surrounding tissue trajectory.

Figure 1A:
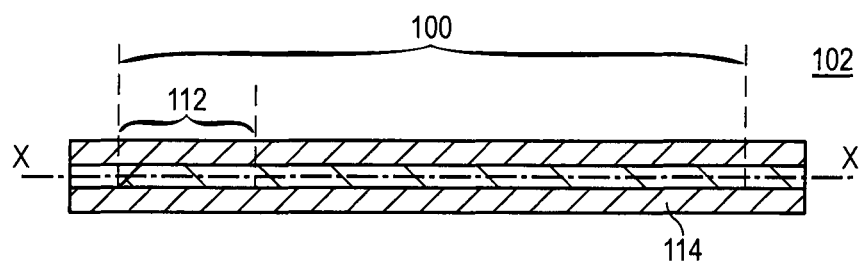
FIG. 1A shows a side view of a vascular access device in accordance with an embodiment.

FIG. 1A shows a side view of the vascular access device 102 in accordance with an embodiment. The vascular access device 102 may include a needle 100 having a tip portion 112; and a shield 114 arranged around and at least substantially along a longitudinal axis (X-X) of the needle 100, wherein the shield 114 is substantially rigid so as to provide strength to the tip portion 112 to penetrate the tissue layer as the tip portion 112 extends out from the shield 114 and the needle 100 gradually loses column strength or conforms to the surrounding tissue beneath the tissue layer as the distance between the tip portion 112 and the shield 114 increases. In this regard, the inherent property of the needle 100 does not change between the position where the needle 100 is housed within the shield 114 and the position when the needle 100 is out of the shield 114. The change in state of the needle 100 or the loss in column strength is a result of the needle 100 moving out from the shield 114, thereby losing the rigidity which is provided by the shield 114.

The needle 100 is substantially elongated and may be of approximately the same length as the shield 114 or may be slightly shorter than the length of the shield 114, depending on the user design and requirements. Further, the needle 100 may be sized in diameter so as to fit appropriately within the interior of the shield 114. If the diameter of the needle 100 is sized very close to or larger than the diameter of the shield 114, there may be some resistance or difficulty in sliding or moving the needle 100 relative to the shield 114. Therefore, the diameter of the needle 100 may be appropriately chosen so as to provide an ease of the needle 100 sliding within and out of the shield 114.

In the example shown in FIG. 1A, surrounding the flexible needle shaft 100 is the rigid translatable tubular support sheath or shield 114 of an inner diameter slightly larger than an outer diameter of the flexible needle shaft 100. An 18 G needle 100 has an edge to edge width (or outer diameter) of about 1.270 mm and an 14 G needle 100 has an edge to edge width of about 2.108 mm.

Further, the tip portion 112 may include a substantially sharp portion configured to allow ease of the penetration of the tissue layer. The sharper the tip portion 112, the easier the needle 100 may be allowed to be pierced through the tissue layer. If the tip portion 112 is too blunt, there may be some difficulty in piercing through the tissue layer and may cause some pain to the user.

The outer diameter of the needle 100 may be in a range of between 1.270 mm (18 G) to 2.108 mm (14 G) and the length of the needle 100 required to interact with the guiding portion (shown later in FIG. 5A) may be in a range of between about 3 mm to 12 mm. Also, the thickness of the material forming the shield 114 may be in the range of between about 0.1 mm to 0.3 mm. These values may be consistent with the wall thickness of the 26 G and 13 G rigid needle 100. Typically, the thicker the material used to form the shield 114, the more rigid is the shield 114. This rigidity of the shield 114 is also dependent on the material used to form the shield 114. The thickness and material of the shield 114 may be dependent on user and design requirements.

Figure 1B:
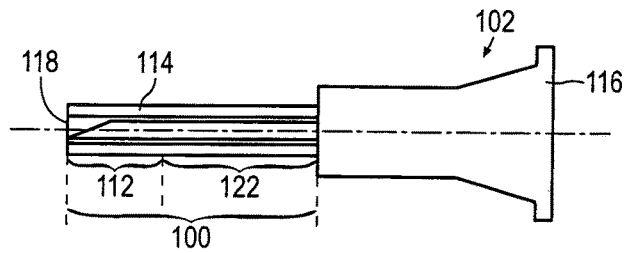
FIG. 1B shows a side view of a vascular access device with an actuating portion, where a needle is fully encapsulated within a shield in a sterile chamber in accordance with an embodiment.
Figure 1C:
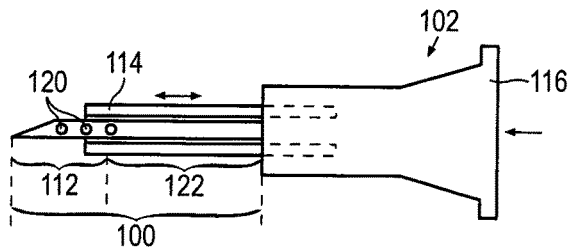
FIG. 1C shows a side view of the needle which pierces a seal positioned at a distal end of the shield while the sheath moves towards the actuating portion in accordance with an embodiment.
Figure 1D:
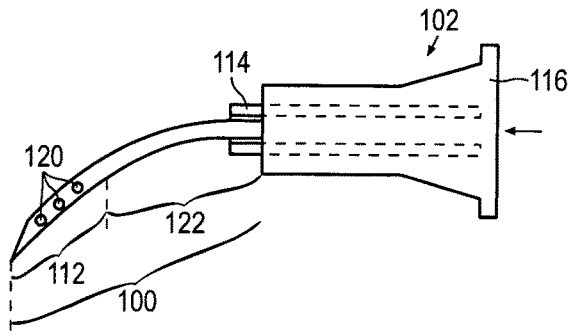
FIG. 1D shows a side view of the needle with substantially no column strength when the rigid support sheath is fully retracted within the actuating portion in accordance with an embodiment.

FIGS. 1B to 1D show respective side views of the vascular access device 102 in various stages of use from a initial starting position in FIG. 1B to an intermediate position which allows piercing of a skin layer in FIG. 1C and to a use position where the needle 100 is fully extended within the blood vessel (not shown) in FIG. 1D.

In more details, FIG. 1B shows a side view of the vascular access device 102 with an actuating portion 116, where the needle 100 is fully encapsulated within the shield 114 in a sterile chamber in accordance with an embodiment. FIG. 1C shows a side view of the needle 100 which pierces a seal 118 (shown in FIG. 1B) positioned at a distal end of the shield 114 while the sheath 114 moves towards the actuating portion 116 in accordance with an embodiment. FIG. 1D shows a side view of the needle 100 with substantially no column strength when the rigid support sheath 114 is fully retracted within the actuating portion 116 in accordance with an embodiment.

Like in FIG. 1A, the vascular access device 102 in FIGS. 1B to 1D may include a needle 100 having a tip portion 112; and a shield 114 arranged around and at least substantially along a longitudinal axis (X-X) of the needle 100, wherein the shield 114 is substantially rigid so as to provide strength to the tip portion 112 to penetrate a tissue layer (not shown) as the tip portion 112 extends out from the shield 114 and the needle 100 gradually loses column strength or conforms to the surrounding tissue beneath the tissue layer as the distance between the tip portion 112 and the shield 114 increases.

However, unlike FIG. 1A, the vascular access device 102 in FIGS. 1B to 1D may additionally include the actuating portion 116 coupled to a portion of the needle 100. In FIGS. 1B to 1D, the actuating portion 116 is shown to be coupled to one end of the needle 100, opposite to the tip portion 112. However, the actuating portion 116 may be coupled to at any suitable portion along the needle 100, for example at both sides or just at one side of the needle 100. Also, the actuating portion 116 may be coupled at one point or at a plurality of points along the needle 100 depending on user and design requirements. Further, the shape of the actuating portion 116 may vary depending on user and design requirement.

Further, the shield 114 is substantially rigid so as to provide strength to the tip portion 112 to first penetrate a skin layer (not shown) and then the tissue layer (i.e. subcutaneous tissue layer) (not shown) beneath the skin layer to access a blood vessel (not shown) below the tissue layer when the actuating portion 116 is first actuated and to gradually lose column strength as the shield 114 retracts into the actuating portion 116 and as the needle 100 enters and travels along the blood vessel, so as to prevent the needle 100 from penetrating a further tissue layer beneath the blood vessel.

The shield 114 is configured to be slidable relative to the tip portion 112. As an example in FIG. 1C, the shield 114 may be slidable relative to the tip portion 112 when a force (as shown by the arrow) is applied onto the actuating portion 116. A further force may be applied on the shield 114 so that the respective forces on the actuating portion 116 and the shield 114 may allow the shield 114 to slide into the actuating portion 116. Also, as an example, there may be alignment tracks within the actuating portion 116 for ease of sliding the shield 114 into the actuating portion 116 and to limit the extent in which the shield 114 is able to slide into the actuating portion 116. As an example, the direction of the force on the actuating portion 116 may be as shown in the arrow in FIGS. 1C and 1D. The shield 114 may also be slidable relative to the tip portion 112 without any force applied onto the actuating portion 116.

In an alternative embodiment, the shield 114 may also be slidable by means of a press button or activation means (not shown) positioned at any suitable location on the actuating device 116. The press button may operate together with a spring positioned within the actuating portion 116 such that the spring may be compressed as the shield 114 slides into the actuating portion 116 and to release the shield 114 back to an original default position covering the needle 100 as soon as the user has completed use of the vascular access device 102. In this case, the vascular access device 102 is placed near to the skin layer 104 such that the tip portion 112 of the needle 100 is forced into the skin layer 104 when the outer shield 114 retracts within the actuating device 116.

As shown in FIG. 1B, the shield 114 may further include a sealing portion 118 arranged covering an open end of the shield 14 and adjacent to the tip portion 112 of the needle 100 so as to seal the needle 100 therein a sterile chamber within the shield 114. The tip portion or a distal end 112 of the needle 100 may include a plurality of ports or openings 120 to increase flow rate of fluid flowing into the blood vessel. The higher the number of ports 120, the higher the flow rate of fluid into the blood vessel. The size of each of the ports 120 may also influence the flow rate of fluid into the blood vessel. The ports 120 may be positioned at fixed intervals at the tip portion 112 or may be positioned randomly along the length of the tip portion 112. The ports 120 may also be positioned along the entire length of the needle 100. The number, the size and the position of the ports 112 may vary depending on user and design requirements.

The needle 100 may further include a flexible portion 122, the flexible portion 122 may be coupled directly or indirectly to the tip portion 112. The length of the tip portion 112, the flexible portion 122 or the ratio of the tip portion 112 relative to the flexible portion 122 may vary depending on user and design requirements. The length of the tip portion 112 may be in a range of about 2 mm to 6 mm and the length of the flexible portion 122 may be in a range of about 4 mm to about 20 mm. Further, the diameter of the flexible portion 122 may be substantially consistent with the diameter of the tip portion 112 or may vary depending on user and design requirements. Also, the cross-sectional of the flexible portion 122 and the tip portion 112 may be substantially circular. But any other cross-sectional shapes of the flexible portion 122 and the tip portion 112 are also possible. Further, the tip portion 112 and the flexible portion 122 may be formed as one integrated portion or may be formed from separate portions and coupled together by any suitable couplings. More details on the material of the respective tip portion 112 and flexible portion 122 may be disclosed in the description relating to FIGS. 1F and 1G.

Figure 1E:
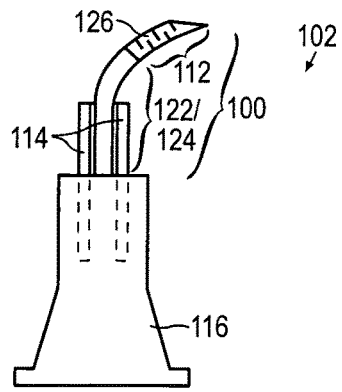
FIG. 1E shows a side view of an alternative embodiment of a vascular access device with a needle constructed by laser cut flexible metallic tubing in accordance with an embodiment.

FIG. 1E shows a side view of an alternative embodiment of a vascular access device 102 with the needle 100 constructed by laser cut flexible metallic tubing 124 in accordance with an embodiment. In FIG. 1E, the needle 100 is shown to be a combination of a laser cut metal needle portion 126 which provides flexibility and porousness of the tip portion 112 (or distal section) to increase flow of the fluid into the blood vessel and a polymer or shrink tube coating 124 along a remaining section of the laser cut needle 126. The portion of the needle 100 which is not covered by the polymer or shrink tube coating 124 may be termed the tip portion 112 of the needle 100 while the portion of the needle 100 which is covered by the polymer or shrink tube coating 124 may be termed the flexible portion 122 of the needle. The polymer or shrink tube coating 124 is configured to fit snugly onto the laser cut metal needle 126 to prevent any sliding of the polymer or shrink tube coating 124 relative to the laser cut metal needle 126. The shield 114 retracts into the actuating portion 116 to a certain extent such that the needle 100 is shown to lose some column strength.

Figure 1F:
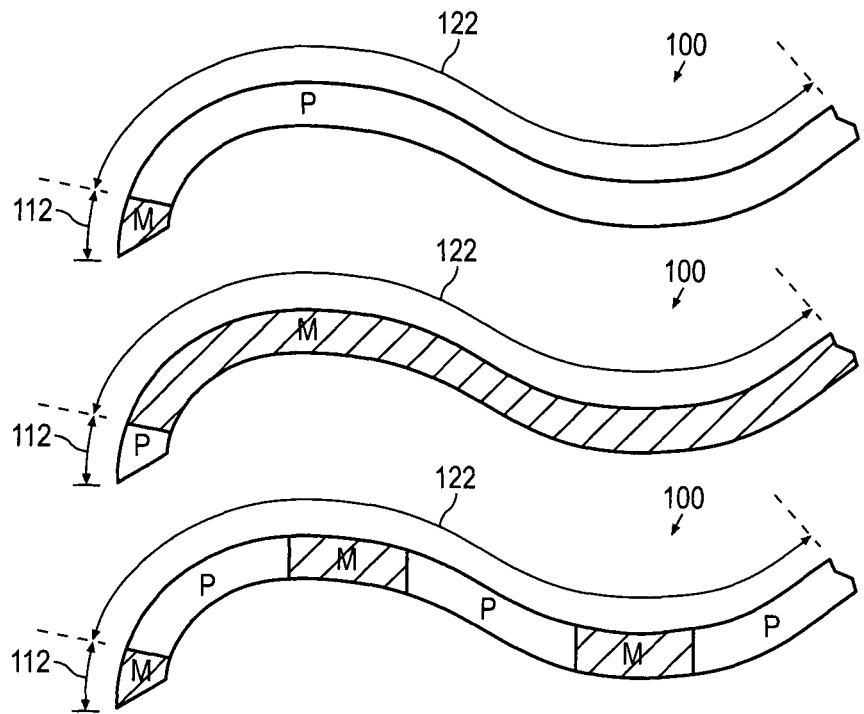
FIG. 1F shows a needle with different material configurations to construct the needle shaft according to an embodiment.

FIG. 1F shows a needle 100 with different material configurations to construct the needle shaft 100 according to an embodiment.

The flexible needle shaft 100 may include a single material or a combination of materials with varying flexibility in order to achieve this desired flexibility. Material configurations may include, but are not limited to a combination of metal and polymer in various permutations. In one embodiment, the flexible portion (or proximal shaft) 122 of the flexible needle 100 is fabricated from polymer and the tip portion (or the distal needle tip) 112 of the flexible needle 100 is fabricated from metal. In another embodiment, the flexible portion (or proximal shaft) 122 of the flexible needle 100 is fabricated from metal and the tip portion (or the distal needle tip) 112 of the flexible needle 100 is fabricated from polymer. In yet another embodiment, the flexible portion 122 of the flexible needle 100 is fabricated from a combination of polymer and metal positioned or coupled in an alternating manner and the tip portion 112 of the flexible needle 100 is fabricated from metal. For example, the flexible portion 122 and the tip portion 112 may also include shape-memory alloys, either alone or in combination with polymer and metal in any suitable configurations. The flexible needle 100 may also be formed of all metal or all polymers.

Figure 1G:
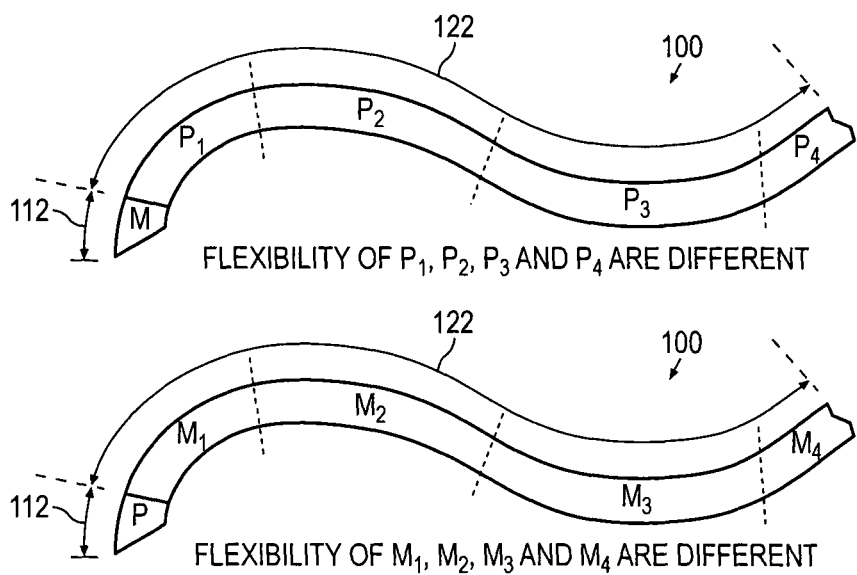
FIG. 1G shows a needle configured with different material flexibility along its longitudinal axis in accordance with an embodiment.

FIG. 1G shows a needle 100 configured with different material flexibility along its longitudinal axis in accordance with an embodiment.

In one embodiment, the flexible needle 100 with the metal tip portion (or distal metal tip) 112 may be constructed with the flexible portion 122 or proximal segment of the needle shaft 100 having polymer with differing flexibility along the longitudinal axis of the needle shaft 100. In another embodiment, the flexible needle 100 can be constructed with a polymer needle tip or tip portion 112 coupled with a laser-cut metal proximal shaft or flexible portion 122. Similarly, the proximal metal shaft or flexible portion 122 can be configured to have differing flexibility along the longitudinal axis of the needle 100. Conceivably, the proximal shaft or the flexible portion 122 of the flexible needle 100 may also be constructed with alternatively segments of laser-cut metal and flexible polymers to achieve the desired flexibility and push-strength.

The polymer to metal interface may be bonded by use of bio-adhesives that may be UV or time cured (such as Dymax or Loctite), heat treatment, chemical bonding, mechanical interlocking mechanism or a combination of adhesives or heat with sandblasted metal surfaces. Bonding materials should be inert and unreactive to body fluids and range of medical fluids with which the bonding materials may come in contact. In some embodiments, flexible needle shaft 100 may be coated with lubricious material with low coefficient of friction to allow a smoother navigation through the buttonhole. Such coating includes, but not limited to Polytetrafluorethylene (PTFE), polyurethane (PU), polyethylene (PE) and high density polyethylene.

Figures 2A, 2B, 2C:
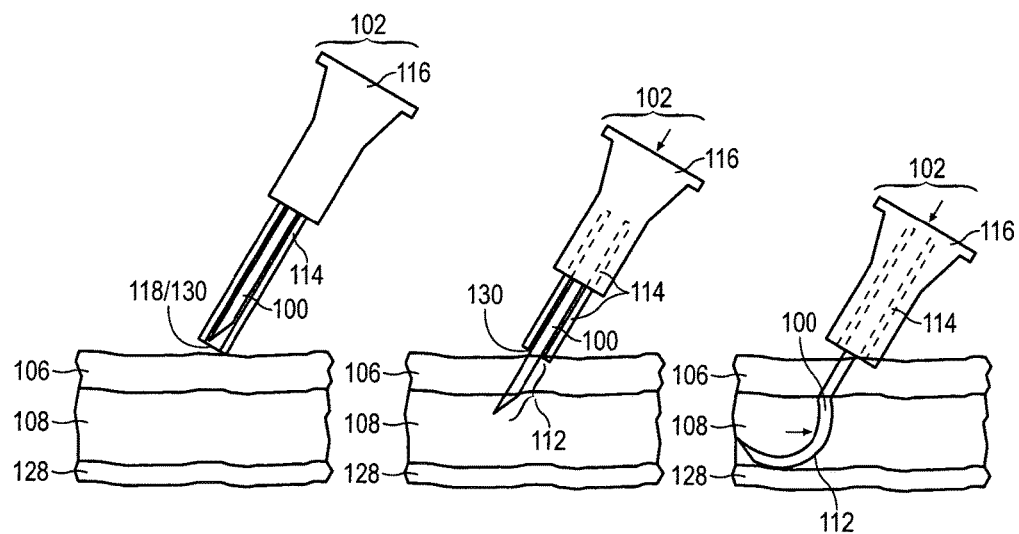
FIG. 2A shows a side view of a vascular access device with a needle within a sterile environment before the seal breaks in accordance with an embodiment.
FIG. 2B shows a side view of the vascular access device with the needle with column strength to penetrate a tissue layer in accordance with an embodiment.
FIG. 2C shows a side view of the vascular access needle unable to penetrate a subsequent layer of tissue without column strength in accordance with an embodiment.

FIGS. 2A to 2C illustrate the principle of the vascular access device 102, applied in obtaining access to a blood vessel 108, and how this device 102 may enable safer vascular access.

FIG. 2A shows a side view of a vascular access device 102 with a needle 100 within a sterile environment before the seal 118 breaks in accordance with an embodiment, FIG. 2B shows a side view of the vascular access device 102 with the needle 100 with column strength to penetrate a tissue layer 106 in accordance with an embodiment, FIG. 2C shows a side view of the vascular access needle 100 unable to penetrate a subsequent layer of tissue 128 without column strength in accordance with an embodiment.

In FIG. 2A, the support sheath 114 prevents the flexible needle shaft 100 from buckling when the needle tip or tip portion 112 has not travelled beyond a distal opening 130 of the support sheath 114. This enables the flexible access needle 100 to have column strength to penetrate the first layer of tissue or subcutaneous tissue layer 106. In FIG. 2B, upon the tip portion 112 of the flexible access needle 100 travelling beyond the distal opening 130 of the support sheath 114, the protruded section or tip portion 112 of the flexible needle shaft 100 loses side support from the rigid sheath 114, thereby losing column strength. Subsequently, as seen in FIG. 2C, further pushing of the tip portion 112 of the needle 100 to a second layer of tissue 128 causes the flexible needle shaft 100 to buckle, thereby losing force transmission ability and penetrative force. The direction of force onto the actuating portion 116 is as shown in the arrows in FIGS. 2B and 2C. The device 102 will work as long as the tip portion 112 is sharp and has enough force transmission to penetrate the first layer of tissue or subcutaneous tissue layer 106.

Figure 3A:
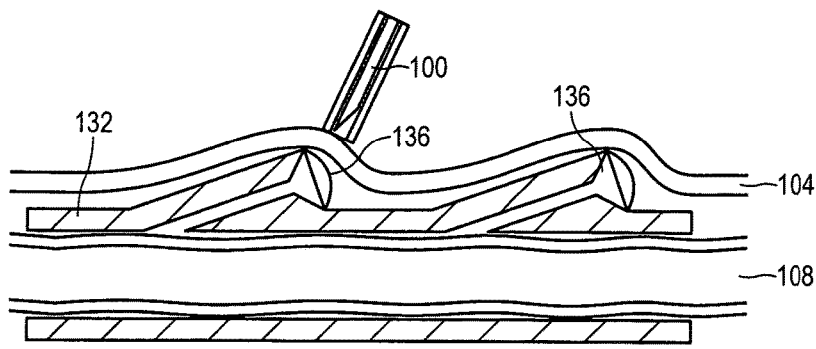
FIG. 3A shows a side cross-sectional view of a fistula with a vascular access cuff implanted extraluminally in accordance with an embodiment.

FIGS. 3A to 3F show how the vascular access needle 100 interacts with a vascular access cuff 132. FIG. 3A shows a side cross-sectional view of a fistula or blood vessel 108 (an abnormal connection or passageway between two epithelium-lined organs or vessels that normally do not connect) with the vascular access cuff 132 implanted extraluminally in accordance with an embodiment. In FIG. 3A, the vascular access cuff 132 is shown to include 2 subsurface ports 136 branching from the cuff 132 that encompasses a blood vessel 108, such as a fistula or vascular graft. Although FIG. 3A shows 2 subsurface ports 136, there may be more than 2 subsurface ports 136 depending on user and design requirements. Each port 136 creates a "bump" on the skin layer 104.

Figure 3B:
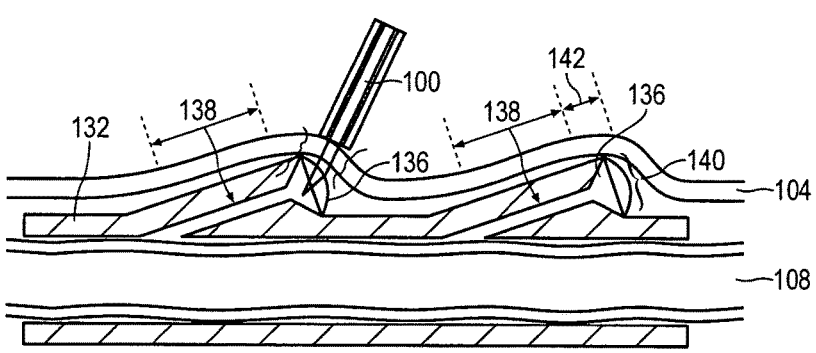
FIG. 3B shows a side cross-sectional view of the fistula with the vascular access needle penetrating a skin layer and entering a port of the vascular access cuff in accordance with an embodiment.
Figure 3C:
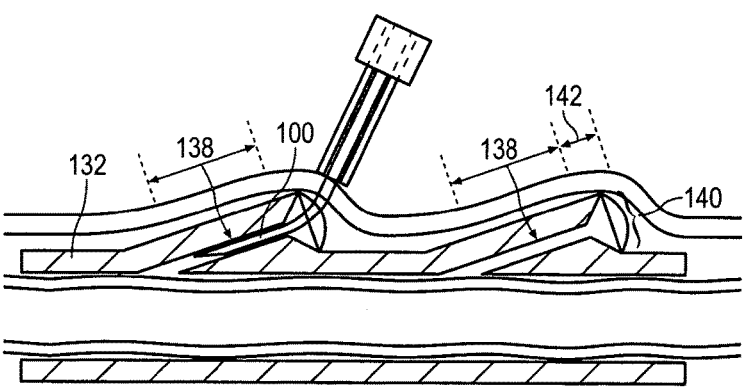
FIG. 3C shows a side cross-sectional view of the fistula with the vascular access needle entering a support tunnel of the vascular access cuff in accordance with an embodiment.

FIG. 3B shows a side cross-sectional view of the fistula or blood vessel 108 with the vascular access needle 100 penetrating a skin layer 104 and entering a port 136 of the vascular access cuff 132 in accordance with an embodiment and FIG. 3C shows a side cross-sectional view of the fistula or blood vessel 108 with the vascular access needle 100 entering a support tunnel 138 of the vascular access cuff 132 in accordance with an embodiment.

A patient identifies the "bump" and pierces the vascular access needle 100 through the skin layer 104 directed at the subsurface port 136. The flexible access needle 100, upon penetrating the skin layer 104, pierces through a port membrane 140 and enters a funnel chamber 142. Regardless of the angle the needle 100 enters a funnel chamber 142 of the port 136, the funnel chamber 142 will guide the flexible needle 100 through the support tunnel 138 where the flexible access needle 100 regains support and column strength as shown in FIG. 3B and FIG. 3C.

Figure 3D:
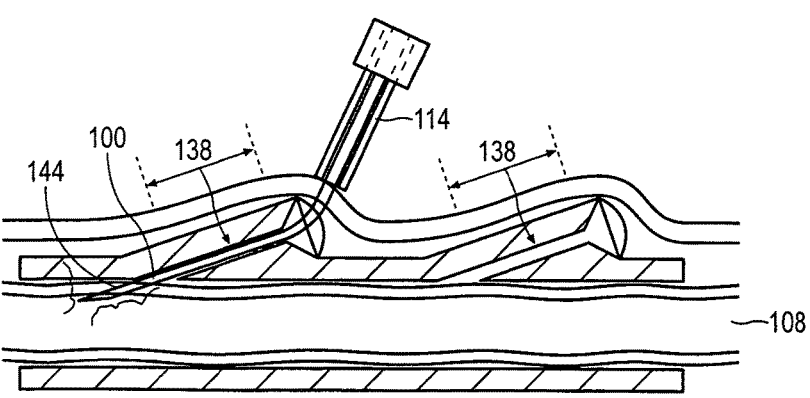
FIG. 3D shows a side cross-sectional view of the fistula with the vascular access needle penetrating a first wall of a vessel to gain vascular access in accordance with an embodiment.

FIG. 3D shows a side cross-sectional view of the fistula or blood vessel 108 with the vascular access needle 100 penetrating a first wall of the vessel 108 to gain vascular access in accordance with an embodiment. Identical to the rigid support sheath 114 in the vascular access needle 100, the support tunnel 138 has an inner diameter slightly larger than the outer diameter of the flexible needle shaft 100 (between 1.270 mm for 18 G needle to 2.108 mm for 14 G needle) to provide the flexible access needle force transmission and penetration strength to pierce through the first wall of the blood vessel 108 when the needle 100 leaves a distal end 144 of the support tunnel 138 as shown in FIG. 3D.

Figure 3E:
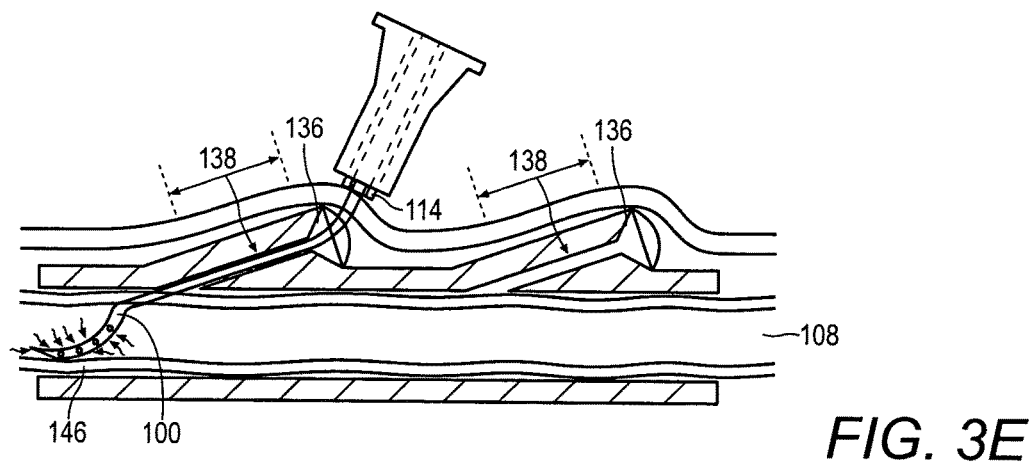
FIG. 3E shows a side cross-sectional view of the fistula with the vascular access needle losing column strength and not traumatizing the adjacent wall of the vessel in accordance with an embodiment.

FIG. 3E shows a side cross-sectional view of the fistula or blood vessel 108 with the vascular access needle 100 losing column strength and not traumatizing the adjacent wall 146 of the vessel 108 in accordance with an embodiment. Upon flexible access needle 100 gaining intraluminal access to the blood vessel 108, the needle 100 loses column strength due to the absence of the rigid sheath support 114 or the support tunnel 138. This allows the flexible access needle 100 to thread in an intra-luminal fashion instead of piercing through an opposite wall 146 of the vessel 108. The user could alternate between subsurface access ports 136 to allow time for the punctured site of the blood vessel 108 to heal.

Figure 3F:
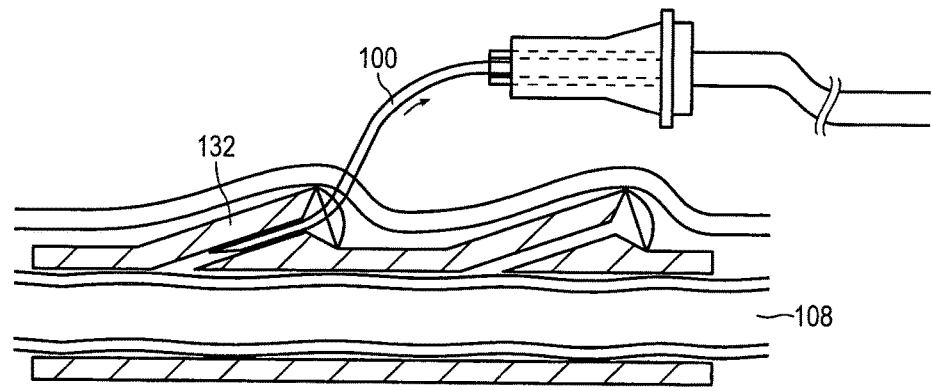
FIG. 3F shows a side cross-sectional view of the fistula with the vascular access needle being extracted out of the vascular access cuff in accordance with an embodiment.

FIG. 3F shows a side cross-sectional view of the fistula or blood vessel 108 with the vascular access needle 100 being extracted out of the vascular access cuff 132 in accordance with an embodiment.

Figure 4A:
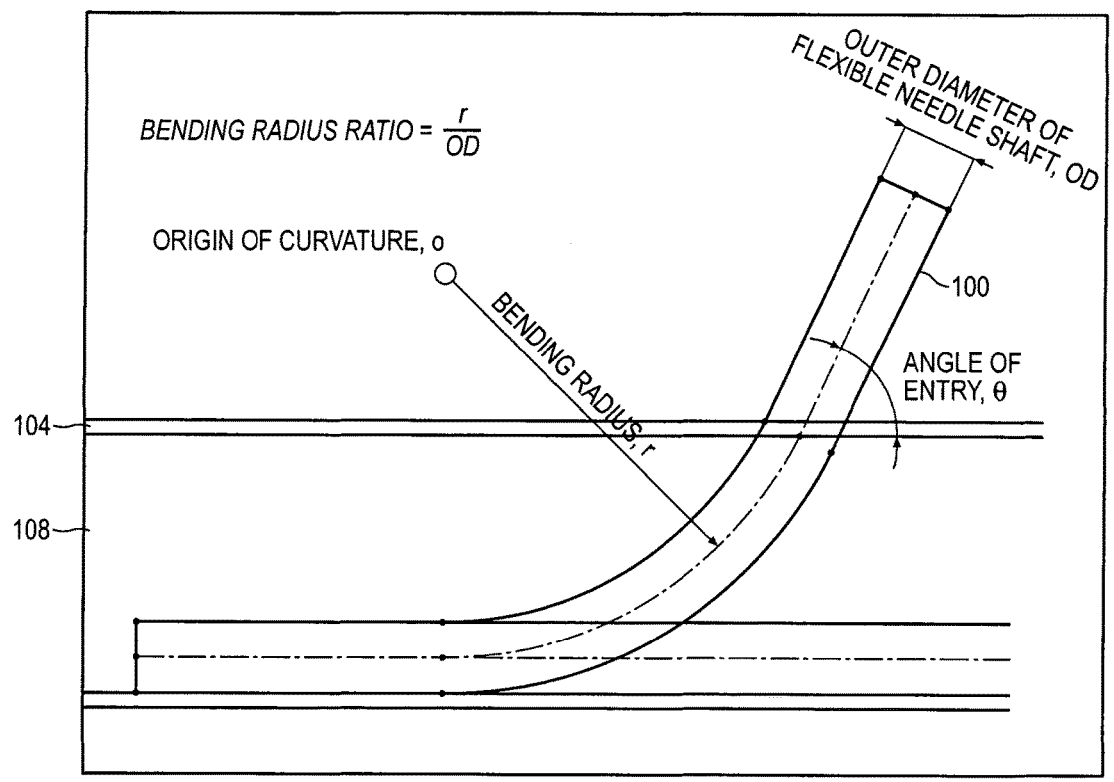
FIG. 4A shows a definition of bending radius ratio and relation with bending radius (r) and an outer diameter (OD) of a needle in accordance with an embodiment.
Figure 4B:
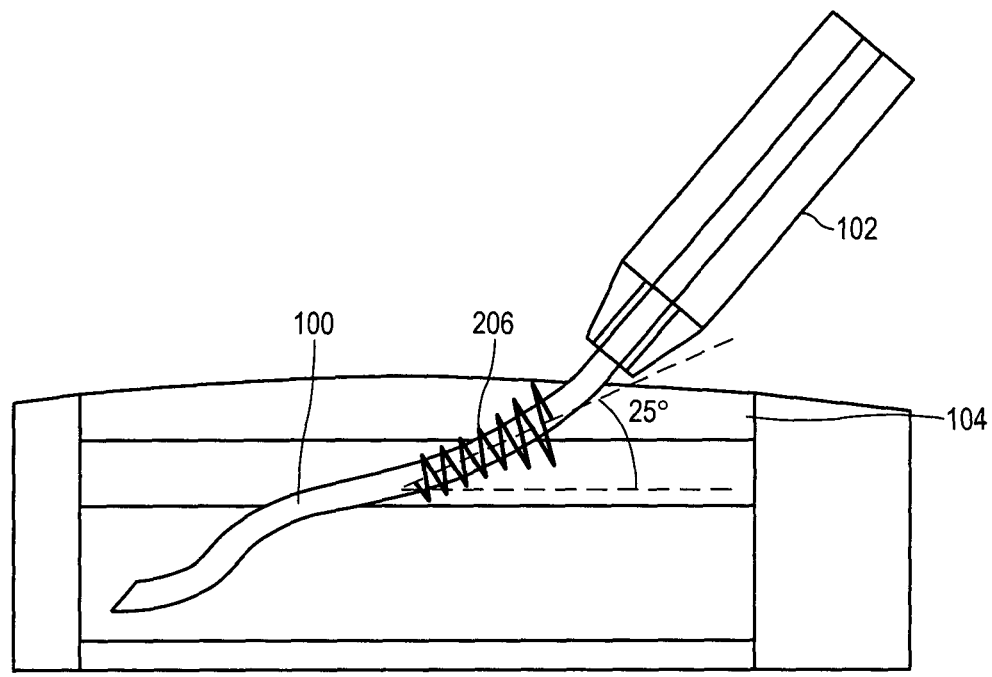
FIG. 4B shows respective cross-sectional view of an entry of a needle through an implanted biodegradable funnel at 25° and 65° in accordance with an embodiment.
Figure 4B:
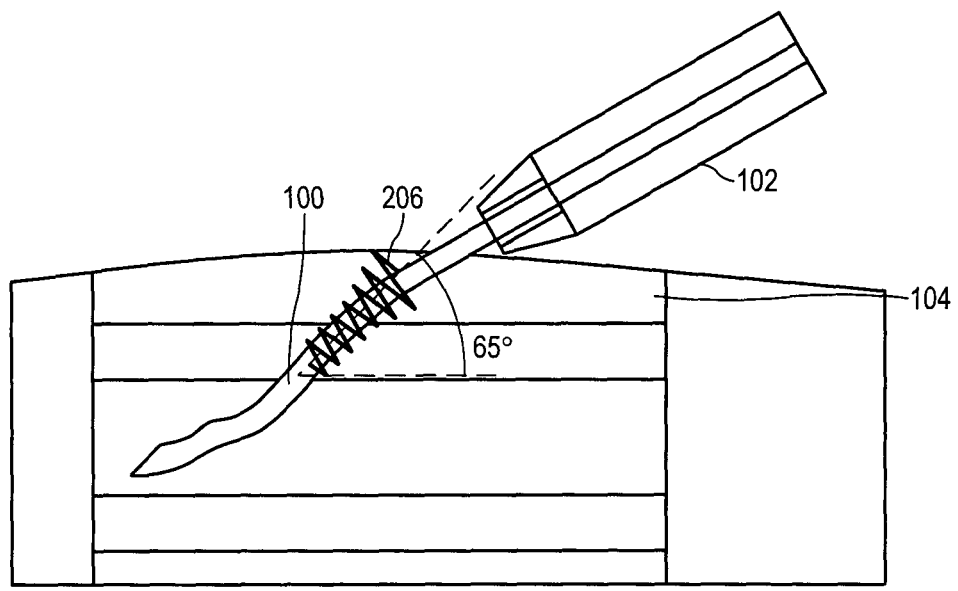

FIGS. 4A to 4B characterize the flexibility of the needle shaft 100 required for the vascular access device 102 (shown in FIG. 1A) to work optimally with the funnel or channel portion (shown later in FIG. 4B or 5A) and in obtaining access to the arteriovenous fistula or blood vessel 108. FIG. 4A shows a definition of bending radius ratio and relation with bending radius (r) and an outer diameter (OD) of a needle 100 in accordance with an embodiment.

FIG. 4A shows a flexible needle shaft 100 of a vascular access device (not shown) relative to a skin layer 104. A portion of the needle shaft 100 is shown to be positioned at an angle relative to the skin layer 104. The angle at which the needle shaft 100 penetrates the skin layer 104 relative to a plane of the skin layer 104 is termed the angle of entry, θ, of the flexible needle shaft 100. The angle of entry, θ may range between more than 0° and less than 90°.

Further, the degree of flexibility of the flexible needle shaft 100 of the vascular access device 104 is defined by the bending radius ratio. The bending radius ratio may be defined as a ratio of the bending radius (r) of the flexible needle shaft 100 to the outer diameter (OD) of the flexible needle shaft 100. The bending radius (r) is measured from a point of the origin of curvature (o) to a centre of the outer diameter (OD) of the flexible needle shaft 100. The outer diameter (OD) of the flexible needle shaft 100 may be taken to be the thickness of the needle shaft 100 or a cross-sectional of the needle shaft 100 in a direction perpendicular to a longitudinal axis of the needle shaft.

For the needle shaft 100 to have a sufficient flexibility, the bending radius (r) may be in the range of 4.8 mm to 56 mm and the outer diameter (OD) of the needle 100 may be in the range of 1.270 mm (18 G) to 2.108 mm (14 G). For example, the outer diameter (OD) of the needle 100 shall be smaller than the diameter of a blood vessel 108 shown beneath the skin layer 104 so as to allow the needle 100 to travel with ease along the blood vessel 108.

FIG. 4B shows respective cross-sectional view of an entry of a needle 100 through an implanted biodegradable funnel or channel portion 206 at about 25° and about 65° relative to the plane of the skin layer 104 in accordance with an embodiment. As an example shown in FIG. 4B, the flexible needle shaft 100 of the vascular access device 102 may be configured to have flexibility of at least 4 times bending radius ratio (upper limit—most flexible), but not more than 44 times bending radius ratio (lower limit—least flexible). As an example, 4 times bending radius ratio indicates that in the most extreme scenario, where vascular access is done in the most unreasonable manner permissable, the needle shaft 100 need not be more flexible than this to enter, hence setting the upper limit. In this regard, 44 times bending radius ratio applies to the scenario in which vascular access is gained in the most optimal case, whereby the needle shaft 100 has to possess at least this flexibility in order to work in this system. As a comparison, a stiff needle shaft 100 which has a bending radius ratio greater than 44 (infinite in this case) may not work.

This flexibility range is optimized to work for the vascular access angle made by either an implanted funnel or channel portion 206 or a buttonhole track (not shown) (or its equivalent) at the angle of entry, θ between about 25° to about 65°. In this regard, the bending radius ratio and the angle of entry may not be confined to the example provided and may vary according to user and design requirements. More details of the implanted funnel or channel portion 206 and the buttonhole track will be described in the description relating to FIGS. 5A to 5P, FIGS. 6A to 6L. FIGS. 7A to 7B, FIGS. 8A to 8P.

Figure 5A:
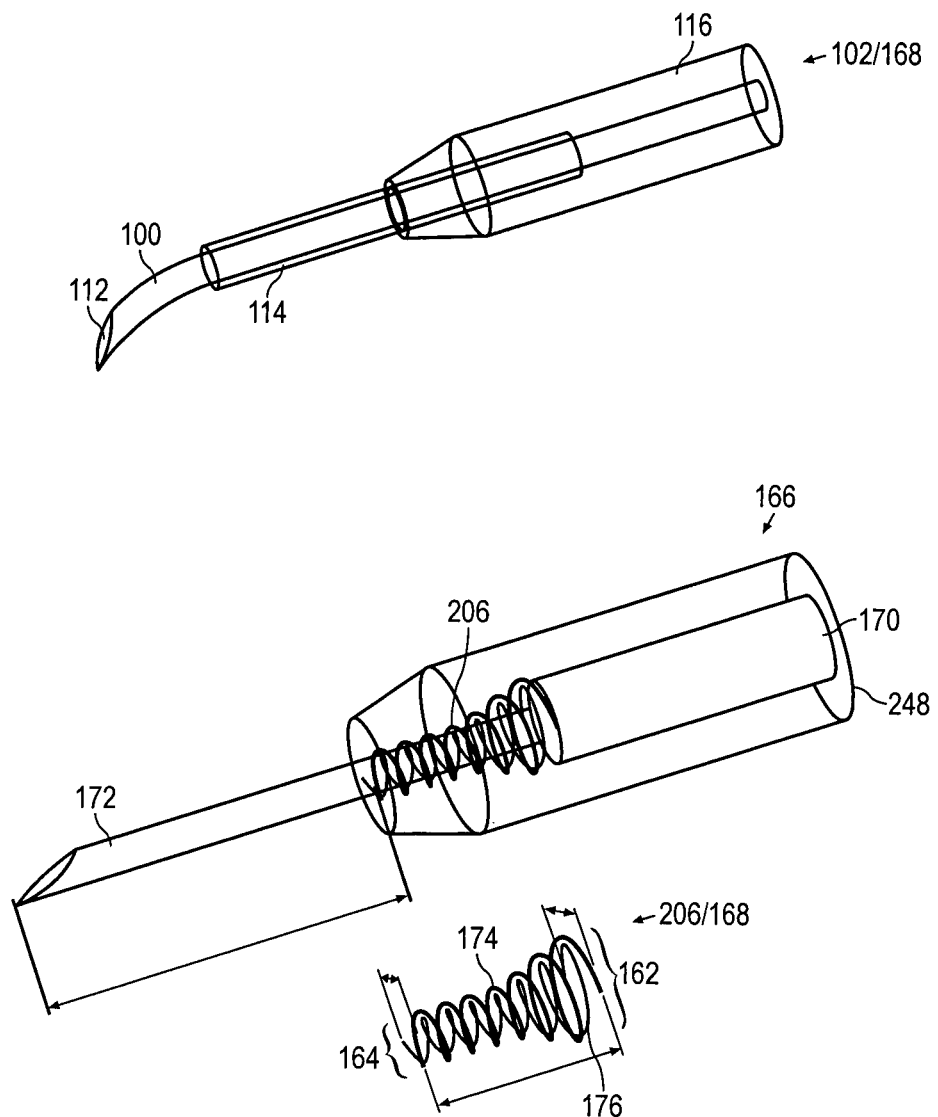
FIG. 5A shows a 3-dimensional view of a vascular access device, a delivery device that inserts a biodegradable funnel, and a close-up view of the implanted funnel in accordance with an embodiment.
Figure 5B:
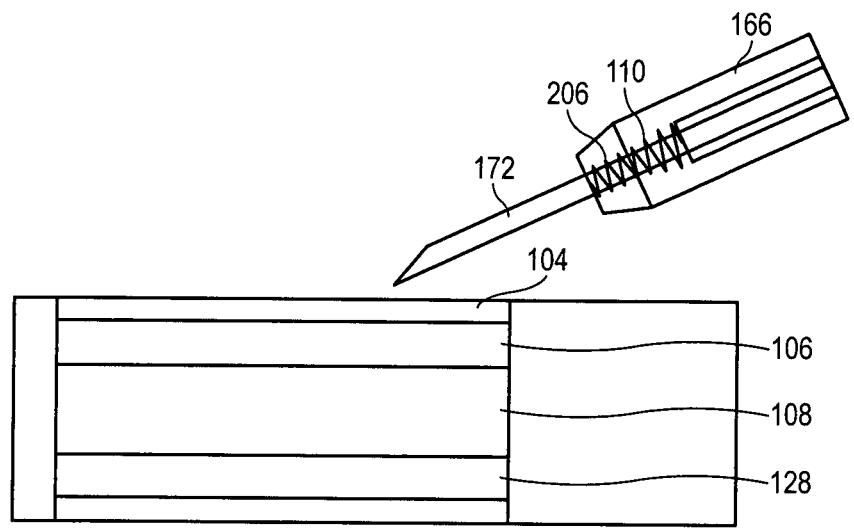
FIG. 5B shows a cross-sectional side view of the delivery device that inserts the biodegradable funnel in accordance with an embodiment.
Figure 5C:
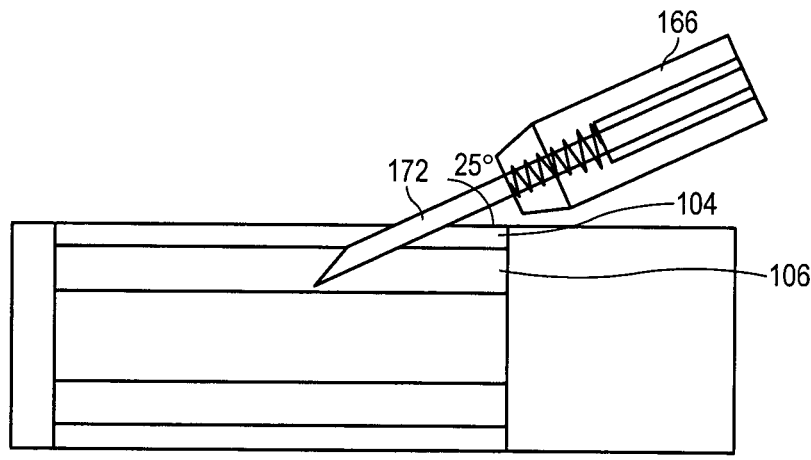
FIG. 5C shows a cross-sectional side view of the delivery needle of the delivery device positioned at an optimal angle of needle insertion in accordance with an embodiment.
Figure 5D:
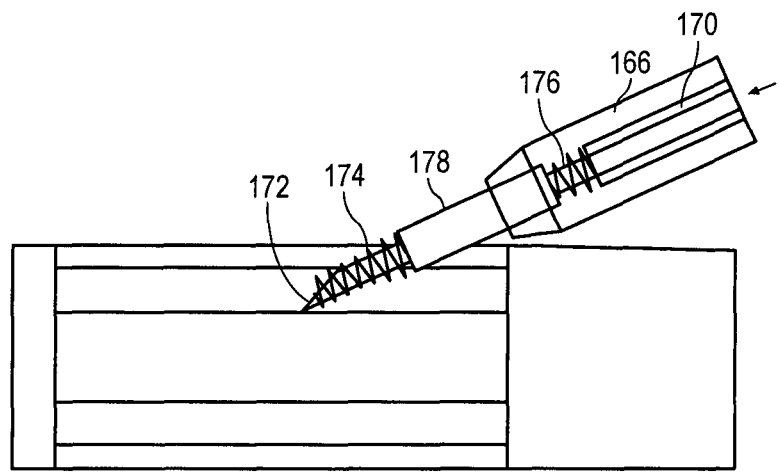
FIG. 5D shows a deployment of a clockwise helical-screw while an anticlockwise helical-screw is still within the delivery device in accordance with an embodiment.
Figure 5E:
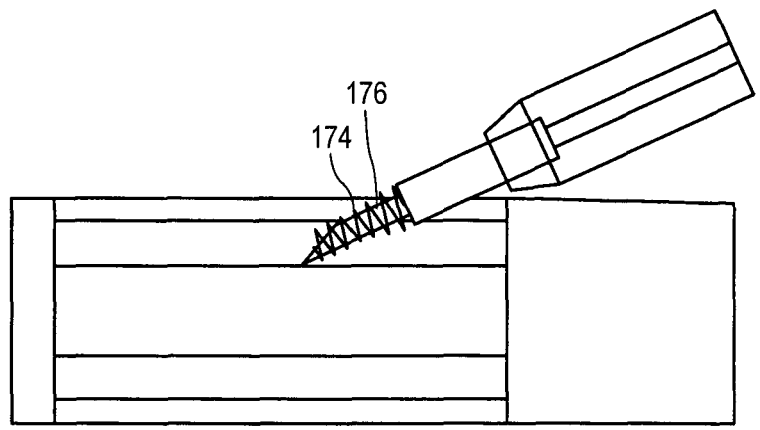
FIG. 5E shows a deployment of the anticlockwise helical-screw with the clockwise helical-screw as a guide in accordance with an embodiment.
Figure 5F:
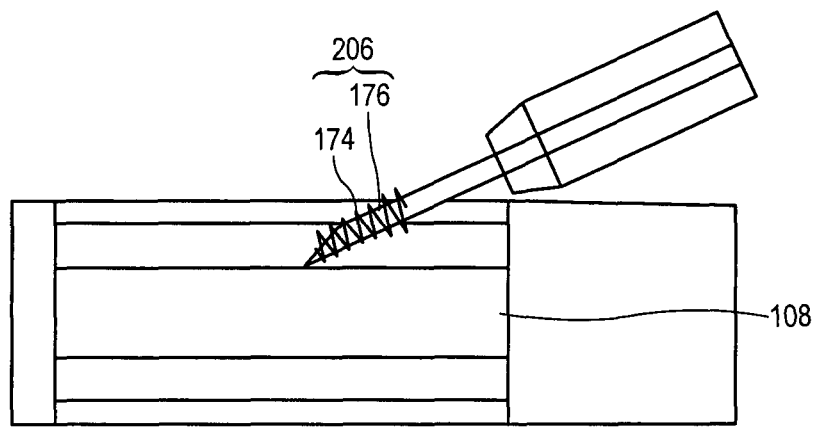
FIG. 5F shows a cross-linking of the clockwise helical-screw and the anticlockwise helical-screw, forming a helical-screw track in accordance with an embodiment.
Figure 5G:
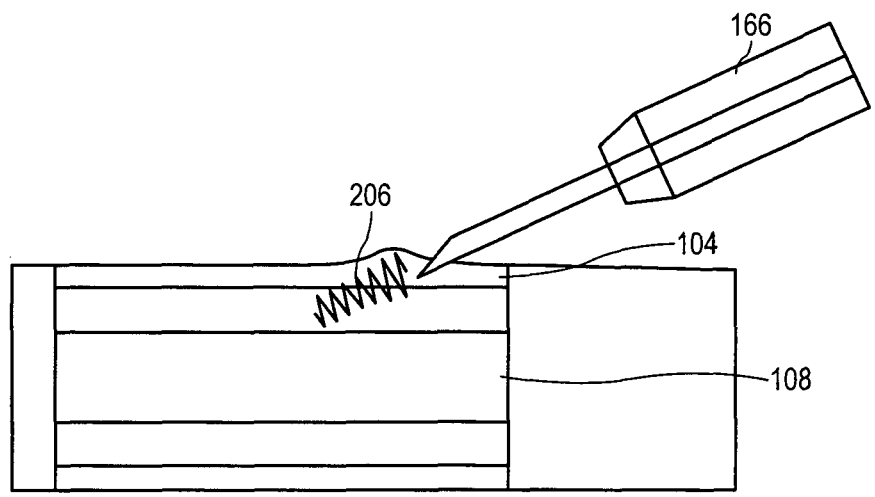
FIG. 5G shows a retraction of the delivery device, leaving behind the helical-screw track in accordance with an embodiment.
Figure 5H:
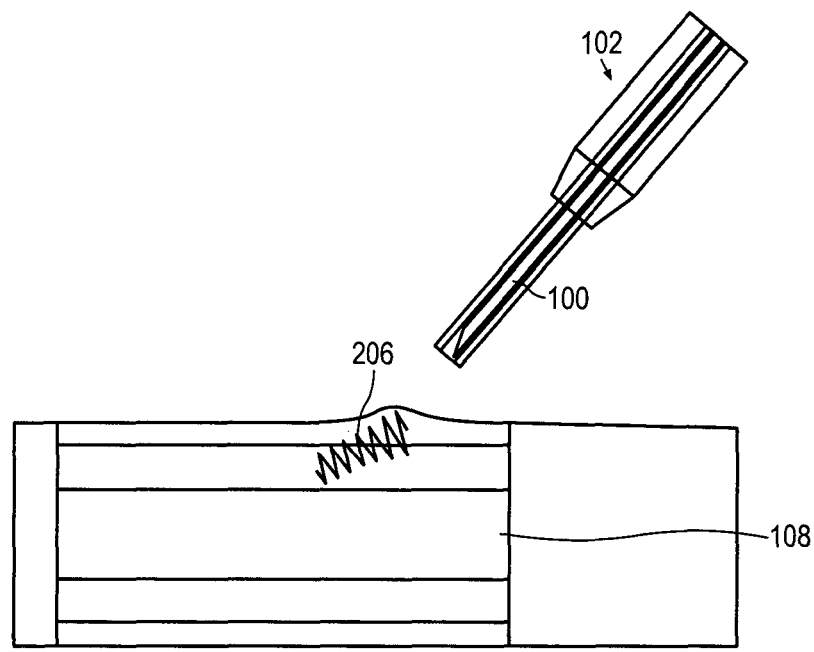
FIG. 5H shows a cross-sectional side view of an implanted helical-screw track and a vascular access device in accordance with an embodiment.
Figure 5I:
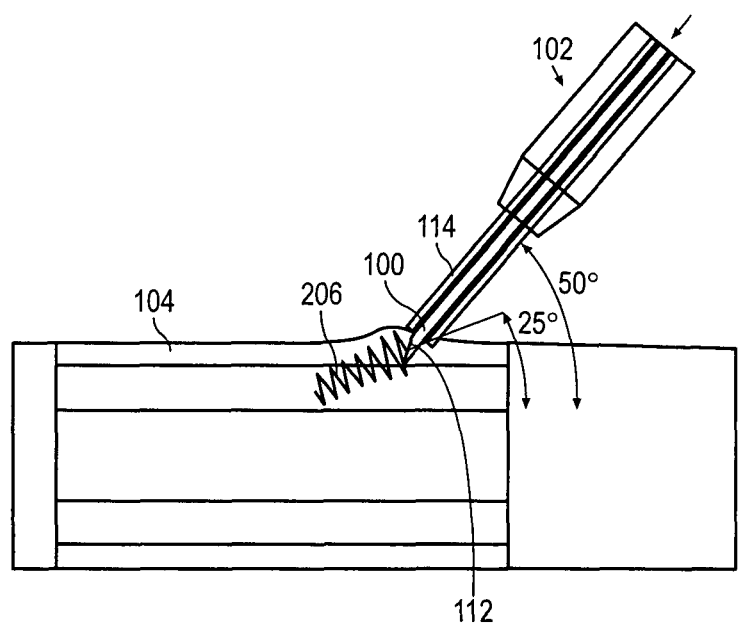
FIG. 5I illustrates cannulation at an incorrect angle by an untrained operator but vascular access device will have the desired push force needed to penetrate the skin layer in accordance with an embodiment.
Figure 5J:
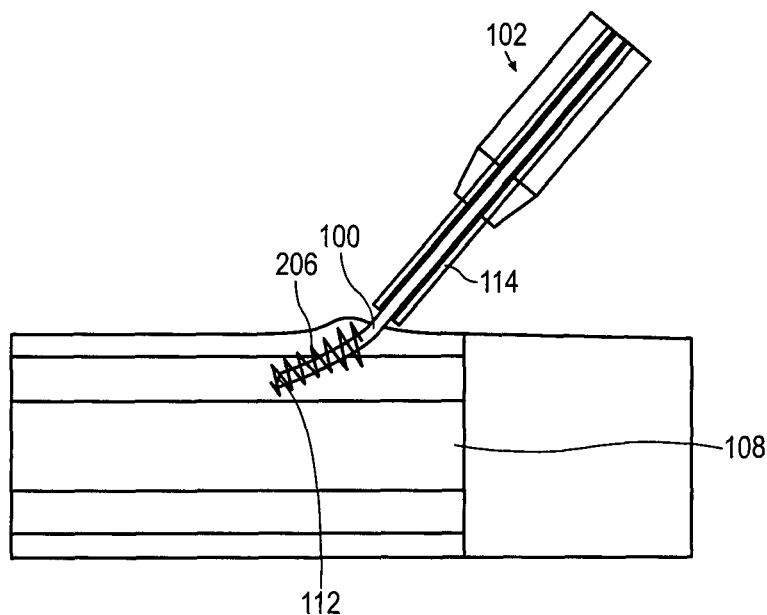
FIG. 5J illustrates a needle which loses push force and conforms to the helical-screw track in accordance with an embodiment.
Figure 5K:
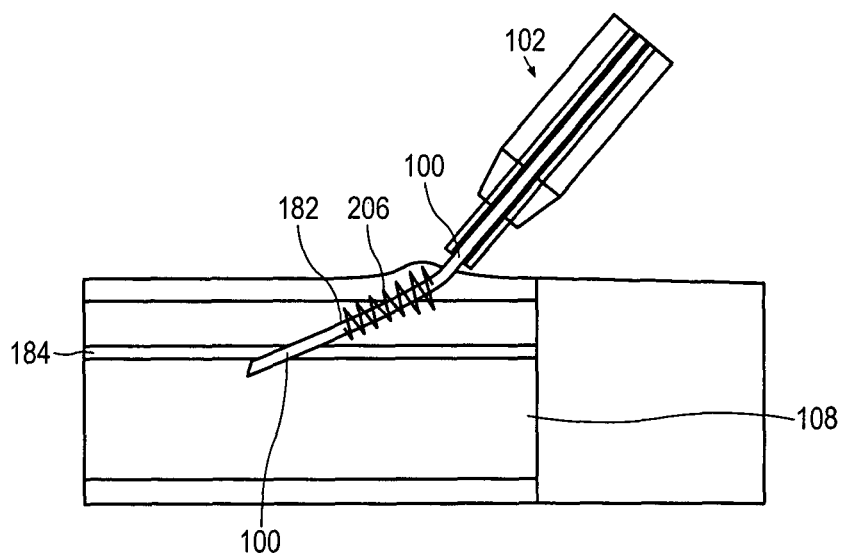
FIG. 5K illustrates a constriction at a distal end of the helical-screw track which causes the needle to regain push force needed to penetrate anterior vein wall (AVF) wall in accordance with an embodiment.
Figure 5L:
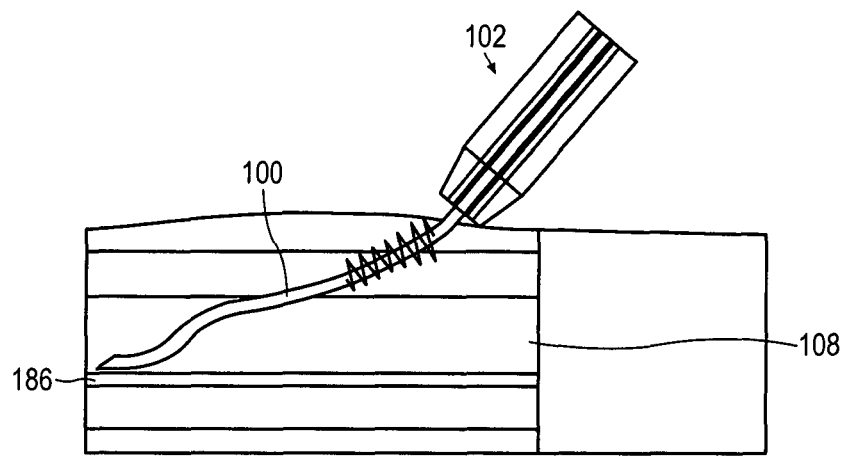
FIG. 5L illustrates the needle which loses push force once in the AVF vessel, allowing the needle to conform to the shape of the vessel, preventing infiltration in accordance with an embodiment.
Figure 5M:
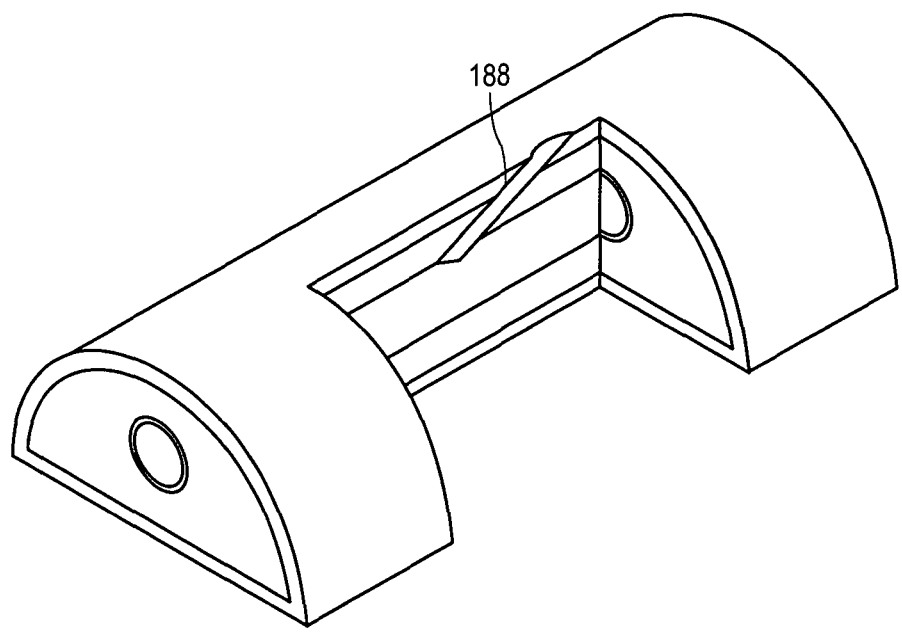
FIG. 5M shows a 3-dimensional cross-sectional side view of the BT track after the helical-screw track dissolves after 2 months in accordance with an embodiment.
Figure 5N:
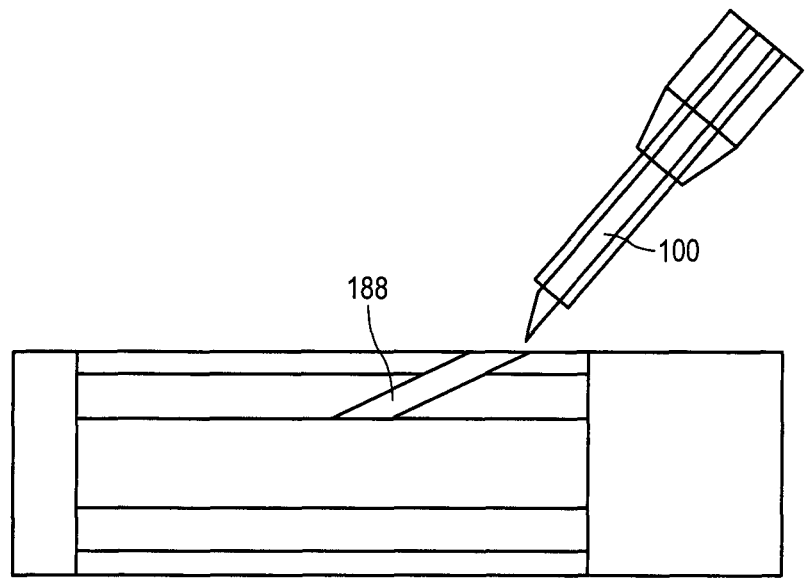
FIG. 5N shows a cross-sectional side view of a track formed by tissue scarring after the helical-screw track is resorbed and a vascular access needle used for the purpose of dialysis in accordance with an embodiment.
Figure 5O:
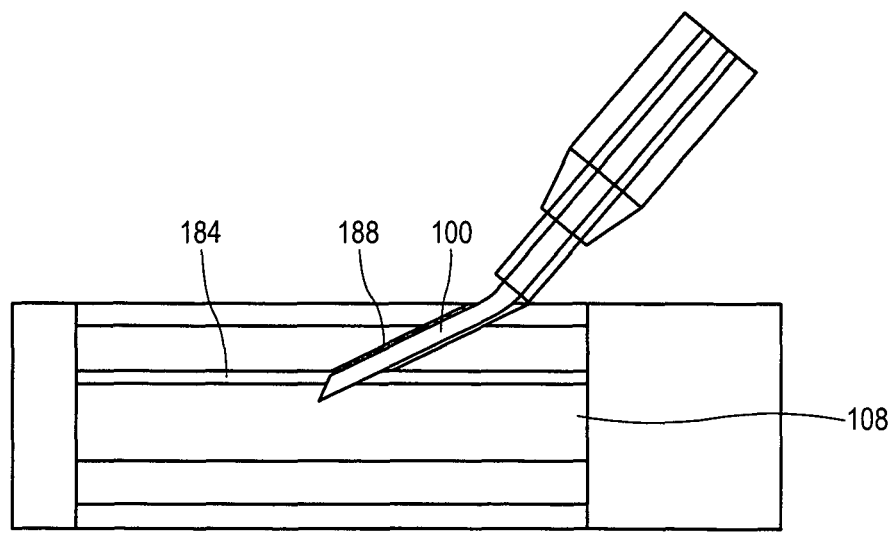
FIG. 5O shows a cross-sectional side view of the flexible needle accessing the AVF through the matured buttonhole in accordance with an embodiment.
Figure 5P:
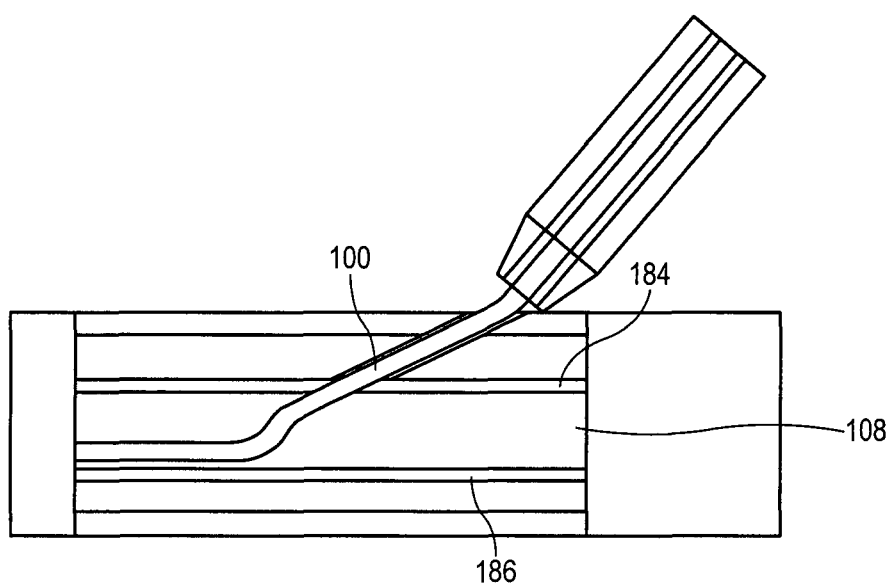
FIG. 5P shows a cross-sectional side view of the flexible needle conforming to the contour of the AVF wall without infiltration in accordance with an embodiment.

FIGS. 5A to 5P illustrate an alternative embodiment where the vascular access cuff 132 as shown in FIGS. 3A to 3F can be substituted with a guiding portion or biodegradable funnel or channel portion 206 (illustrated as a helical-screw track in this instance) that may serve as a guide during needle insertion.

In this regard, the substitution of the vascular access cuff 132 as shown in FIGS. 3A to 3F with the funnel or channel portion 206 removes the requirement for implantation of a foreign body indefinitely while retaining the concept of a single-track creation for needle insertion.

The funnel or channel portion 206 may be defined as a structure that may include a larger inner diameter at the top (entry point or inlet) 162 and a smaller inner diameter at the bottom (exit point or outlet) 164 to guide the needle 100 towards a desired same point of entry of a blood vessel. Funnel construction may be preferred to be biodegradable and resorbable. Materials may include, but may not be limited to: polylactides, polyglycolide, polycaprolactone, random copolymers of polyglycolide and polylactide, random copolymer of lactide and caprolactone. The funnel or channel 206 may also be constructed from a blend of the above-mentioned materials. In some embodiments, biodegradable additives may be used to modify funnel properties such as strength, flexibility and degradation rate. Additives may include, but not limited to: alkyl citrates such as triethyl citrate (TEC), triacetin and polyethylene gycol (PEG). Materials for the non-biodegradable funnel or channel portion 206 may include, but not limited to: thermoplastic elastomer such as silicone rubber and nylon block copolymers. The funnel or channel portion 206 may include pore patterns of any shape, size and pattern that may encourage altered rate of fibrosis on the inner lumen surface. In some embodiments, exterior and interior surfaces of the funnel or channel portion 206 may be modified to have a rough finish so as to promote an altered rate of fibrosis.

The funnel or channel portion 206 interacts as an accessory to a general needle to support track formation in the tissue subcutaneous layer. The purpose of the funnel or channel portion 206 may be to guide the needle through a tunnel, leading to the opening of a blood vessel, such as a fistula or a vascular graft. The port or entry point proximal to the skin has an inner diameter of between about 1.270 mm to about 2.108 mm for the entry of needles 14 G to 18 G. The shape of the funnel or channel portion 206 may include an inverted taper to provide sufficient guidance of the needle 100 towards the blood vessel, with features such as, but not limited to a unidirectional valve at the end of the taper, gel filled cavity in the tapered funnel and a dog-bone shaped saddle support.

Figure 6A:
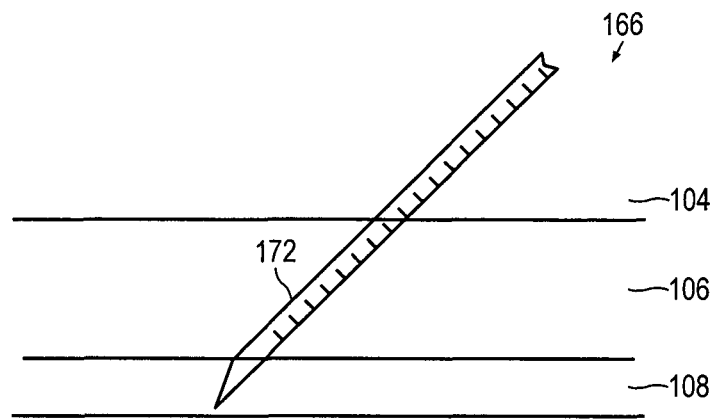
FIG. 6A shows a cross-sectional side view of a delivery needle of a funnel delivery device with ruler marking on the needle in accordance with an embodiment.

FIG. 5A shows a 3-dimensional view of a vascular access device 102, a delivery device 166 that inserts a biodegradable funnel or channel portion 206, and a close-up view of an implanted funnel or channel portion 206 in accordance with an embodiment. In FIG. 6A, the vascular access device 102; and the implanted funnel or the channel portion 206 may form the vascular access system 168.

The vascular access device 102 in FIG. 5A is similar to that shown in FIG. 1B. Like in FIG. 1B, the vascular access device 102 in FIG. 5A may include a needle 100 having a tip portion 112; and a shield 114 arranged around and at least substantially along a longitudinal axis (not shown) of the needle 100, wherein the shield 114 is substantially rigid so as to provide strength to the tip portion 112 to penetrate a tissue layer (not shown) as the tip portion 112 extends out from the shield 114 and the needle 100 gradually loses column strength as the distance between the tip portion 112 and the shield 114 increases. The vascular access device 102 may additionally include an actuating portion 116 coupled to a portion of the needle 100.

The delivery device 166 is similar to the vascular access device 102 in that the delivery device 166 includes a delivery actuating portion 170 and a delivery needle 172 coupled to the delivery actuating portion 170. However, the delivery needle 172 is relatively rigid compared to the flexible needle 100 of the vascular access device 102. The funnel or channel portion 206 to be inserted into the patient is to be initially housed within a handle 248 of the delivery device 166.

In FIG. 5A, the biodegradable funnel or channel portion 206 includes two helical-screw tracks 174 (dark line), 176 (light line), one in the clockwise direction and the other in the anticlockwise direction. These two helical-screw tracks 174, 176 may be inserted with the delivery device 166 prior to vascular needle access. Depending on the mechanism of the funnel delivery device 166, each helical-screw 174, 176 may be inserted sequentially or at the same time. In the event that the biodegradable funnel or channel portion 206 does not include more than 1 part, the entire funnel or channel portion 206 may be delivered in a single instance by the funnel delivery device 166.

In FIG. 5A, the implementation of two anti-directional helical-screws 174, 176 may serve as a track or funnel that guides future needle insertions. The length of the funnel or channel portion 206 to be used may be predetermined in accordance with the distance the intended blood vessel is from the surface of the skin layer. As an example, the length of the funnel or channel portion 206 may range between about 3 mm to about 12 mm. The funnel or channel portion 206 is expected to be absorbed over time (e.g. about 1-6 months), leaving a scarred tissue track 188 as shown in FIG. 5N that serves as a track for future needle insertions.

FIGS. 5B to 5G illustrates how the funnel or channel portion 206, which includes two helical-screws 174, 176, is inserted with the delivery device 166.

FIG. 5B shows a cross-sectional side view of the delivery device 166 that inserts the biodegradable funnel or channel portion 206 in accordance with an embodiment. The delivery device 166 with the funnel or channel portion 206 pre-stored within the delivery device 166 is first brought near to a skin layer 104 of a patient. The respective layers of the patient as shown in FIG. 5B are the outer skin layer 104, a subcutaneous tissue layer or first tissue layer 106 below the skin layer 104, a blood vessel 108 below the subcutaneous tissue layer 106 and a second tissue layer 128 below the blood vessel 108.

FIG. 5C shows a cross-sectional side view of the delivery needle 172 of the delivery device 166 positioned at an optimal angle of needle insertion in accordance with an embodiment. In FIG. 5C, the funnel delivery device 166 is first inserted at the desired angle such that the delivery needle 172 penetrates the skin layer 104 and the subcutaneous tissue layer 106. In FIG. 5C, the angle is shown to be about 25° but this angle can be adjusted according to user and design requirements.

FIG. 5D shows a deployment of a clockwise helical-screw 174 while an anticlockwise helical-screw 176 is still within the delivery device 166 in accordance with an embodiment. In FIG. 5D, an outer delivery sheath 178 of the delivery needle 172 that previously held onto the ends of the helical-screws 174, 176 then ejects the helical-screws 174, 176 (one after the other for example). The outer delivery sheath 178 may be activated by means of a force onto the delivery actuating portion 170 of the delivery device 166 by a push button. However, any other suitable means of activating the outer delivery sheath 178 may also be possible depending on user and design requirements. The outer delivery sheath 178 may be of a relatively rigid material such that any force exerted on the outer delivery sheath 178 may be translated onto the helical-screws 174, 176.

FIG. 5E shows a deployment of the anticlockwise helical-screw 176 with the clockwise helical-screw 174 as a guide in accordance with an embodiment. In FIG. 5E, the clockwise helical-screw 174 is delivered with the anticlockwise helical-screw 176 as a guide. The external diameter of the clockwise helical-screw 174 may be slightly smaller/bigger than the internal diameter of the anticlockwise helical-screw 176 to ensure a good fit. However, the external diameter of the clockwise helical-screw 174 may also be comparable with the external diameter of the anticlockwise helical-screw 176.

FIG. 5F shows a cross-linking of the clockwise helical-screw 174 and the anticlockwise helical-screw 176, forming a helical screw track or channel portion 206 in accordance with an embodiment. The helical-screw track or channel portion 206 is configured to be placed at an angle above the blood vessel 108 and configured to receive and guide a vascular access needle (not shown) to reach the same location of the blood vessel 108 repeatedly and consistently.

FIG. 5G shows a retraction of the delivery device 166 leaving behind the helical-screw track or channel portion 206 in accordance with an embodiment. In FIG. 5G, the funnel delivery device 166 is retracted, leaving behind the funnel or channel portion 206 (that includes both the biodegradable clockwise and anticlockwise helical-screws 174, 176 in this embodiment). The funnel or channel portion 206 forms a resultant scarring track between the blood vessel 108 and the skin layer 104 positioned over the blood vessel 108.

FIG. 5H to FIG. 5M illustrate how the funnel or channel portion 206 serves as a guide for the vascular access needle 100 as disclosed in FIG. 1B to access the blood vessel 108 through the same path each and every time during dialysis till the funnel or channel portion 206 is completely resorbed. The funnel or channel portion 206 is biodegradable and may be resorbed by the body with time (e.g. 1-6 months). During this time, the funnel or channel portion 206 may serve as a guide for subsequent repeated insertions.

FIG. 5H shows a cross-sectional side view of an implanted helical-screw track or channel portion 206 and the vascular access device 102 in accordance with an embodiment. In FIG. 5H, the bioresorbable funnel or channel portion 206 has been successfully implanted and the flexible access needle 100 is used to access the vessel 108.

FIG. 5I illustrates cannulation at an incorrect angle of approach by an untrained operator but the vascular access device 102 will have the desired push force needed to penetrate the skin layer 104 in accordance with an embodiment. The funnel or channel portion 206 is arranged at an angle of about 25° relative to the plane of the skin layer 104 while the vascular access device 102 is arranged at an angle of about 50° relative to the same plane. There is a mismatch between the angle of the funnel or channel portion 206 and the vascular access device 102. Nevertheless, despite the mismatch in angles, the flexible access needle 100 in FIG. 5I, exhibits sufficient push force to penetrate the skin 104 due to the rigid support sheath 114 that surrounds the flexible access needle 100. The cannulation angle need not be the same as the angle in which the funnel or channel portion 206 is implanted, as long as the tip portion 112 of the needle 100 of the vascular access device 102 is within the opening mouth of the bioresorbable funnel or channel portion 206.

FIG. 5J illustrates a needle 100 of the vascular access device 102 which loses push force and conforms to the helical-screw track or channel portion 206 in accordance with an embodiment. In FIG. 5J, the flexible access needle 100 of the vascular access device 102 loses its push force as the needle tip (in other words the tip portion 112) of the needle 100 advances away from the rigid sheath 114 and conforms safely to the bioresorbable funnel or channel portion 206. Despite cannulating at a wrong angle, the bioresorbable funnel or channel portion 206 directs the needle 100 back to the desired trajectory to access the vessel 108 at a consistent puncture site.

FIG. 5K illustrates a constriction at a distal end 182 of the helical-screw track or channel portion 206 which causes the needle 100 to regain push force needed to penetrate an anterior vein wall (AVF) wall 184 in accordance with an embodiment. In FIG. 5K, as the flexible access needle 100 advances to the surface of the blood vessel 108 to be penetrated, the flexible needle 100 regains its push force due to the support of the customized narrowed end of the bioresorbable funnel or channel portion 206 and hence is able to penetrate through the vessel 108.

FIG. 5L illustrates the needle 100 of the vascular access device 102 which loses push force once in the blood vessel or AVF vessel 108, allowing the needle 100 to conform to the shape of the vessel 108, preventing infiltration in accordance with an embodiment. In FIG. 5L, after puncturing into the vessel 108, the flexible access needle 100 then loses its push force once again and conforms safely to the orientation of the vessel 108, preventing infiltration on the opposite wall 186.

FIG. 5M shows a 3-dimensional cross-sectional side view of the Buttonhole track 188 after the helical-screw track dissolves after 1 to 6 months in accordance with an embodiment.

After some time, between about 1 to about 6 months, the bioresorbable funnel or channel portion 206 as shown in FIG. 5L may have been resorbed, leaving behind a resultant scarred track 188 as illustrated in FIG. 5M. Scarring of the track 188 ensues due to repeated vascular access needle insertions. The biodegradable funnel or channel portion 206 as shown in FIG. 5L may also serve as a scaffold for scarring to form.

FIG. 5N shows a cross-sectional side view of the track 188 formed by tissue scarring after the helical-screw track 206 as shown in FIG. 5L is resorbed and a vascular access needle 100 used for the purpose of dialysis in accordance with an embodiment.

In FIG. 5N, the biodegradable funnel (not shown) has been resorbed and what remains is the track 188 formed by scarred tissues. The track 188 will then serve as a guide for future needle insertions. The flexible access needle 100 can similarly be used with the scarred track.

FIG. 5O shows a cross-sectional side view of the flexible needle 100 accessing the AVF 184 through the matured buttonhole 188 in accordance with an embodiment. In FIG. 5O, the scarred tissue track 188 serves as a guide for the vascular access needle 100 to access the vessel 108 through the same path each and every time during dialysis.

FIG. 5P shows a cross-sectional side view of the flexible needle 100 conforming to the contour of the AVF wall 184 without infiltration in accordance with an embodiment. FIG.

5P illustrates how the flexible access needle 100 conforms to the contour of the vessel 108 without infiltration of the opposite wall 186.

In this regard, in FIGS. 5B to 5P, a method to obtain access to a blood vessel 108 underneath a skin layer 104 may be disclosed. The method includes placing a channel portion 206 (or guiding portion) between the blood vessel 108 and the skin layer 104; and configuring the channel portion 206 (or guiding portion) to receive and guide a needle 100 to reach the same location of the blood vessel 108 repeatedly and consistently. The guiding portion channel portion 206 (or guiding portion) may be resorbed over time. Also in FIGS. 5A to 5P, a method to create vascular access track underneath a skin layer 104 may be provided. The method may include placing a channel portion 206 (or guiding portion) between the blood vessel 108 and the skin layer 104; configuring the channel portion 206 (or guiding portion) to receive and guide a needle 100; and forming a resultant scarred track between the blood vessel 108 and the skin layer 104 as the channel portion 206 (or guiding portion) is resorbed over time. Further, placing the channel portion 206 (or guiding portion) between the blood vessel 108 and the skin layer 104 may include inserting a delivery device 166 pre-loaded with the channel portion 206 (or guiding portion) into the skin layer 104; releasing the channel portion 206 (or guiding portion) between the blood vessel 108 and the skin layer 104; and retracting the delivery device 166.

FIGS. 6A to 6L illustrate preferred embodiments of the funnel delivery device 166 and various methods of optimizing funnel deployment.

Figure 6B:
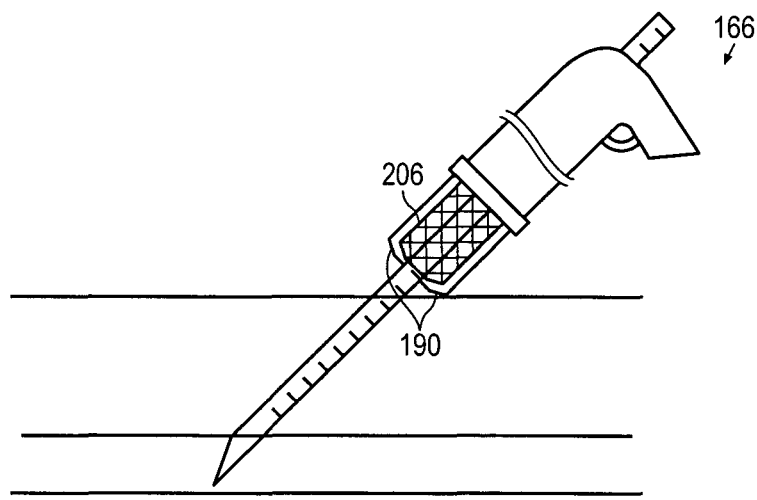
FIG. 6B shows a cross-sectional side view of the funnel delivery device with a funnel of a selected size loaded into the funnel delivery device in accordance with an embodiment.

FIG. 6A and FIG. 6B describe embodiments through which the funnel delivery device 166 is able to determine the depth of tissue beneath the skin 104 and above the blood vessel 108 and then hence deploys the funnel or channel portion 206 of the right size. FIG. 6A shows a cross-sectional side view of a delivery needle 172 of the funnel delivery device 166 with ruler marking on the delivery needle 172 in accordance with an embodiment. In FIG. 6A, the delivery needle 172 with ruler markings is first inserted into the blood vessel 108 through the skin layer 104 and the first subcutaneous layer 106. The visible ruler markings may be engraved, inked, or made via other means either externally or internally to the delivery needle 172. The markings can also be made to become more visible and obvious after flashback of the blood is obtained. Alternatively, tissue depth may be measured electronically through electronic sensors and reported to the user via a digital screen. The tissue depth sensors may include impedance sensors (detecting difference in impendence between air, skin, veins and blood), proximity sensors (detecting length of needle between the handle and above the skin), or heat sensors (detecting difference in temperature of air, skin and blood) or a combination thereof.

FIG. 6B shows a cross-sectional side view of the funnel delivery device 166 with the funnel or channel portion 206 of a selected size loaded into the funnel delivery device 166 in accordance with an embodiment. To deploy a customized-sized funnel or channel portion 206 according to the tissue depth detected, as exemplified by FIG. 6B, the funnel or channel portion 206 of the right length is loaded on the delivery device 166 with the tip of the funnel or channel portion 206 being held onto by a catch 190 on the delivery device 166. Such a funnel or channel portion 206 of the right length may be chosen, then loaded onto the delivery device 166 after the depth of tissue has been determined via a cartridge, pellet, or other means. It may also be accomplished by having a funnel or channel portion 206 of a much longer length that is pre-loaded into the delivery device 166 and then cut at the right length via a built-in mechanism within the delivery device 166 after the depth of tissue or first subcutaneous layer 106 has been determined.

Figure 6C:
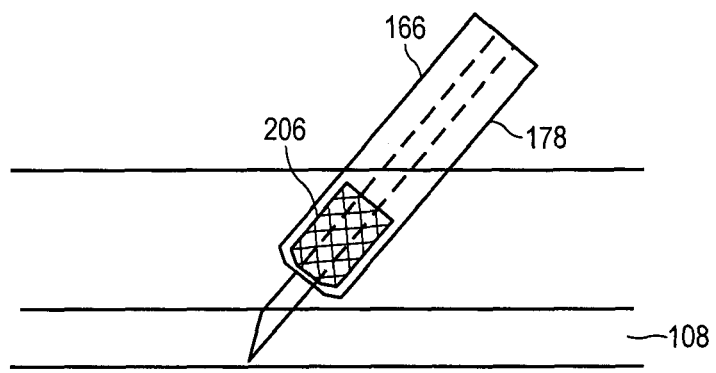
FIG. 6C shows a cross-sectional side view of the funnel delivery device, with the funnel of the selected size loaded in the funnel delivery device, in position for funnel delivery in accordance with an embodiment.
Figure 6D:
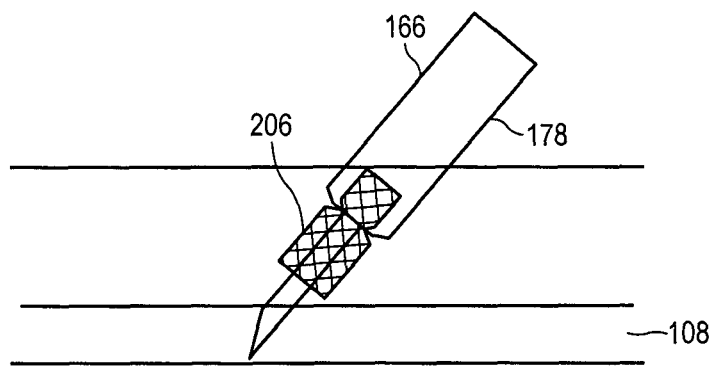
FIG. 6D shows a cross-sectional side view of a sheath of the funnel delivery device being retracted so as to deploy the funnel with shape memory in accordance with an embodiment.
Figure 6E:
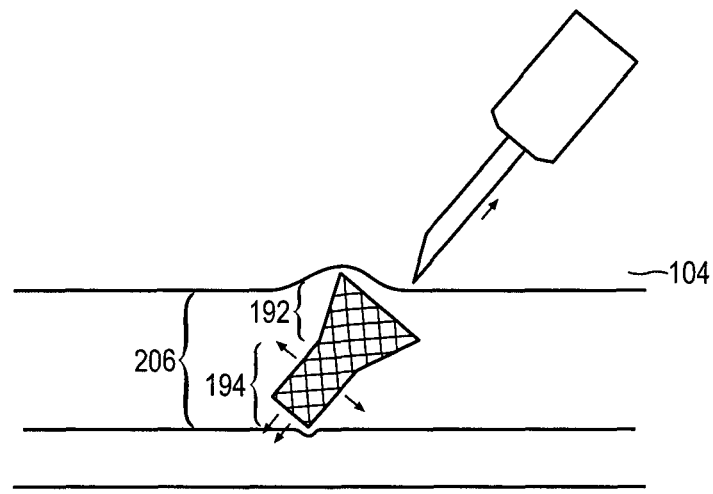
FIG. 6E shows a cross-sectional side view of the funnel being deployed successfully in accordance with an embodiment.

FIGS. 6C to 6F describe the mode of funnel deployment for funnels that possess shape memory properties (meaning ability to remember previous memory shape) and hence self-expandability. In more details, FIG. 6C shows a cross-sectional side view of the funnel delivery device 166, with the funnel or channel portion 206 of the selected size loaded in the funnel delivery device 166, in position for funnel delivery in accordance with an embodiment, FIG. 6D shows a cross-sectional side view of a sheath 178 of the funnel delivery device 166 being retracted so as to deploy the funnel or channel portion 206 with shape memory in accordance with an embodiment, FIG. 6E shows a cross-sectional side view of the funnel or channel portion 206 being deployed successfully in accordance with an embodiment. The funnel or channel portion 206 includes a frusto-conical portion 192 and a tubular portion 194. Essentially the funnel or channel portion 206 includes a porous sidewall with a plurality of holes.

Figure 6F:
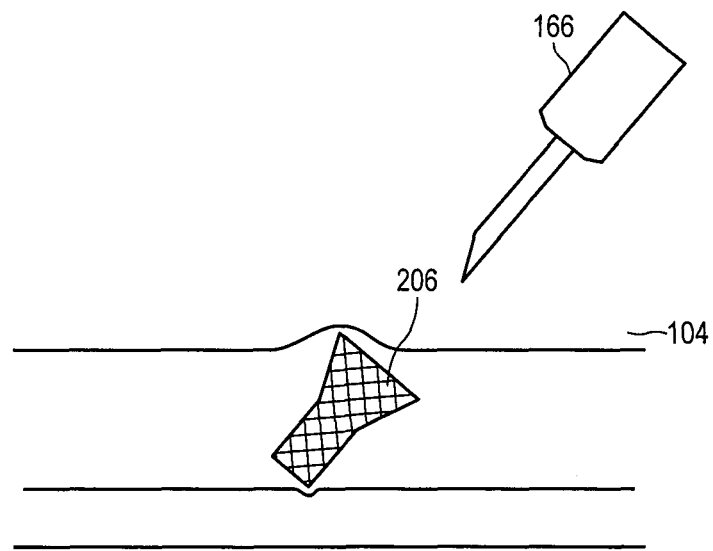
FIG. 6F shows a cross-sectional side view of the funnel delivery device being retracted while leaving the deployed funnel behind in accordance with an embodiment.

FIG. 6F shows a cross-sectional side view of the funnel delivery device 166 being retracted while leaving the deployed funnel or channel portion 206 behind in accordance with an embodiment.

In FIGS. 6B to 6F, the packaged funnel or channel portion 206 is housed within the delivery sheath 178 and deployment is achieved upon retraction of the delivery sheath 178. The funnel or channel portion 206 is packaged in a configuration where the funnel or channel portion 206 expands in both the radial and longitudinal direction upon release of the delivery sheath 178. A successful deployment of the funnel or channel portion 206 may be defined by: first expanding radially so as to achieve an inner lumen that is large enough to accommodate a 14-gauge to 18-gauge vascular access needle; second by expanding longitudinally so as to fit or anchor itself to the vessel 108 in particular by means of push forces in the downward direction, and thirdly expanding longitudinally creating an upward push force to create a bump 204 beneath the skin 104 to serve as a visual and tactile marker to help operators locate the cannulation entry spot for further vascular access.

Figure 6G:
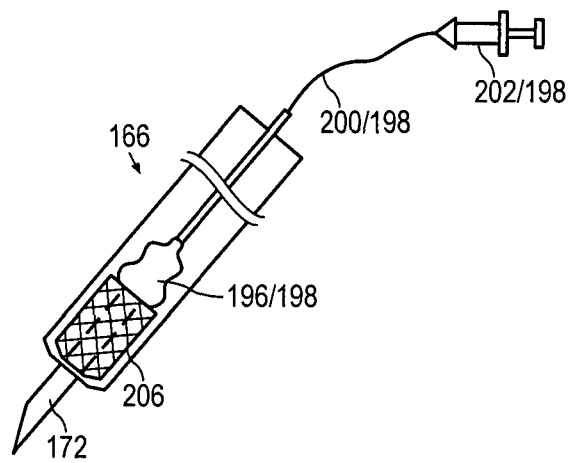
FIG. 6G shows an alternative funnel delivery device for a funnel that does not possess shape memory in accordance with an embodiment.

FIG. 6G shows an alternative funnel delivery device 166 for a funnel or channel portion 206 that does not possess shape memory in accordance with an embodiment.

This mode of funnel deployment for funnels that do not possess shape memory property may be achieved by means of an expandable actuating member such as a balloon 196. The delivery device 166 may include a delivery needle 172 to gain vascular access, a balloon system 198 that includes a balloon 196 and a pressure line 200, a mechanism (for example a simple sheath) that houses the packaged funnel or channel portion 206 around the balloon 196 and a pump 202. Some examples of types of pumps include a saline pump with pressure gauge/dial. Balloon inflates to indicate pressure as user turns the dial. Similar to the way a stent is deployed. The action of the pump 202 may be similar that of a syringe.

FIGS. 6H to 6L describe further steps provided to deploy the funnel 206 successfully using the funnel delivery device 166.

Figure 6H:
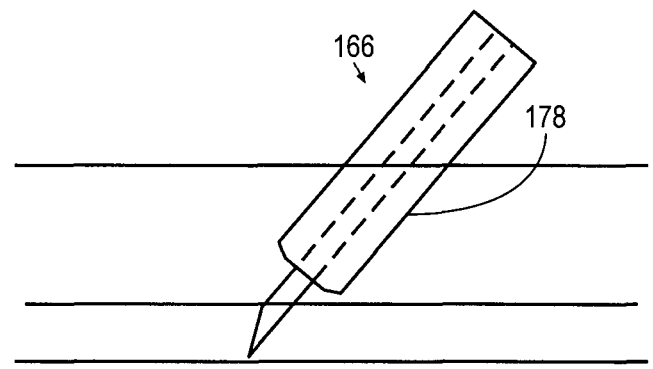
FIG. 6H shows a cross-sectional side view of the funnel delivery device, with a funnel of a selected size loaded in the funnel delivery device, in position for funnel delivery in accordance with an embodiment.
Figure 6I:
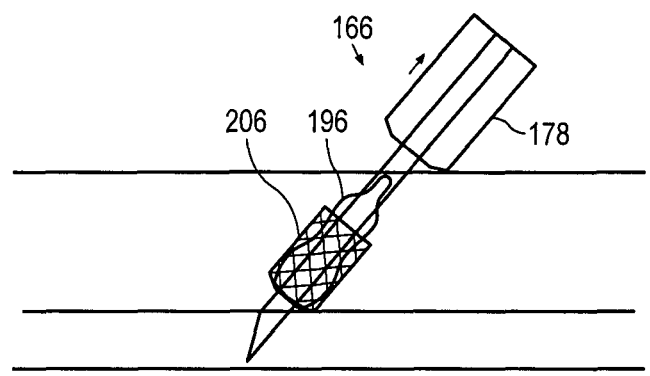
FIG. 6I shows a cross-sectional side view of a sheath of the funnel delivery device being retracted, exposing the packed funnel around a balloon member in accordance with an embodiment.

FIG. 6H shows a cross-sectional side view of the funnel delivery device 166, with a funnel (not shown) of a selected size loaded in the funnel delivery device 166, in position for funnel delivery in accordance with an embodiment, FIG. 6I shows a cross-sectional side view of the delivery sheath 178 of the funnel delivery device 166 being retracted, exposing the packed funnel or channel portion 206 around the balloon member 196 in accordance with an embodiment. After vascular access is achieved in FIG. 6H, the sheath 178 that contains the funnel or channel portion 206 is retracted as shown in FIG. 6I. The packed funnel or channel portion 206 and balloon 196 expand upon being released from the delivery sheath 178.

Figure 6J:
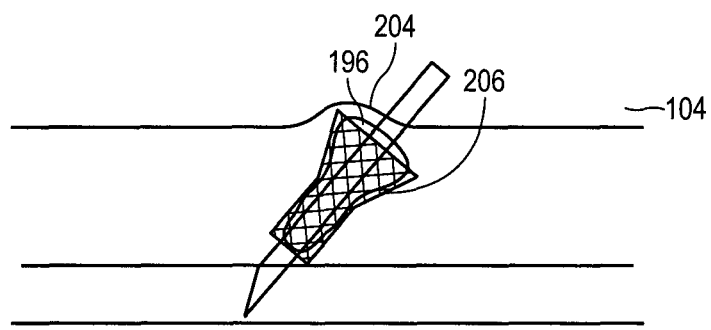
FIG. 6J shows a cross-sectional side view of the balloon member being expanded, thereby expanding the packed funnel, deploying the packed funnel beneath the skin in accordance with an embodiment.
Figure 6K:
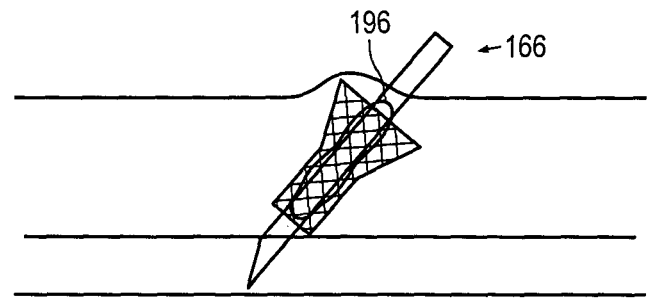
FIG. 6K shows a cross-sectional side view of the balloon member being deflated while the deployed funnel remains in position beneath the skin in accordance with an embodiment.
Figure 6L:
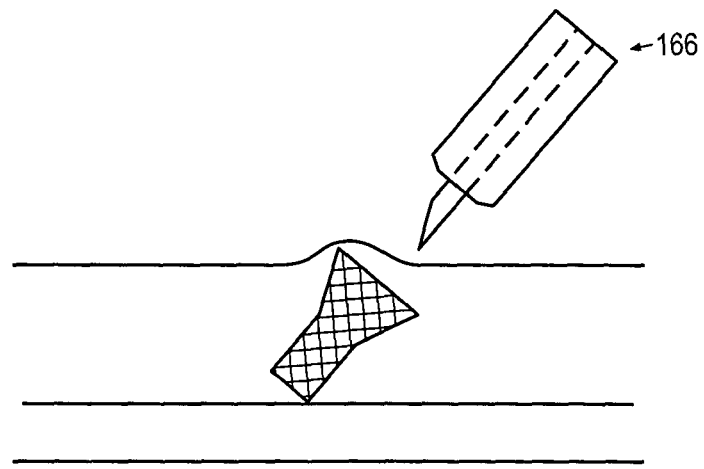
FIG. 6L shows a cross-sectional side view of the funnel delivery device being retracted while leaving the deployed funnel behind in accordance with an embodiment

FIG. 6J shows a cross-sectional side view of the balloon member 196 being expanded, thereby expanding the packed funnel or channel portion 206, deploying the packed funnel or channel portion 206 beneath the skin 104 in accordance with an embodiment, FIG. 6K shows a cross-sectional side view of the balloon member 196 being deflated while the deployed funnel or channel portion 206 remains in position beneath the skin 104 in accordance with an embodiment, FIG. 6L shows a cross-sectional side view of the funnel delivery device 166 being retracted while leaving the deployed funnel or channel portion 206 behind in accordance with an embodiment.

In FIG. 6J, after confirming the position of the funnel or channel portion 206, the balloon 196 is inflated via the pressure line (not shown), hence expanding the packaged funnel or channel portion 206, expanding the funnel or channel portion 206 radially and longitudinally. A successful deployment of the funnel or channel portion 206 may be defined by: first expanding radially so as to achieve an inner lumen that is large enough to accommodate a 14-gauge to 18-gauge needle (not shown); second by expanding longitudinally so as to fit or anchor the funnel or channel portion 206 to the vessel 108 in particular by means of push forces in the downward direction, and third by expanding longitudinally creating an upward push force to create a bump 204 beneath the skin 104 to serve as a visual and tactile marker to help operators locate the cannulation entry spot for further vascular access. The balloon 196 is then subsequently deflated as shown in FIG. 6K and then the entire delivery device 166 is retracted as shown in FIG. 6L.

Figure 7A:
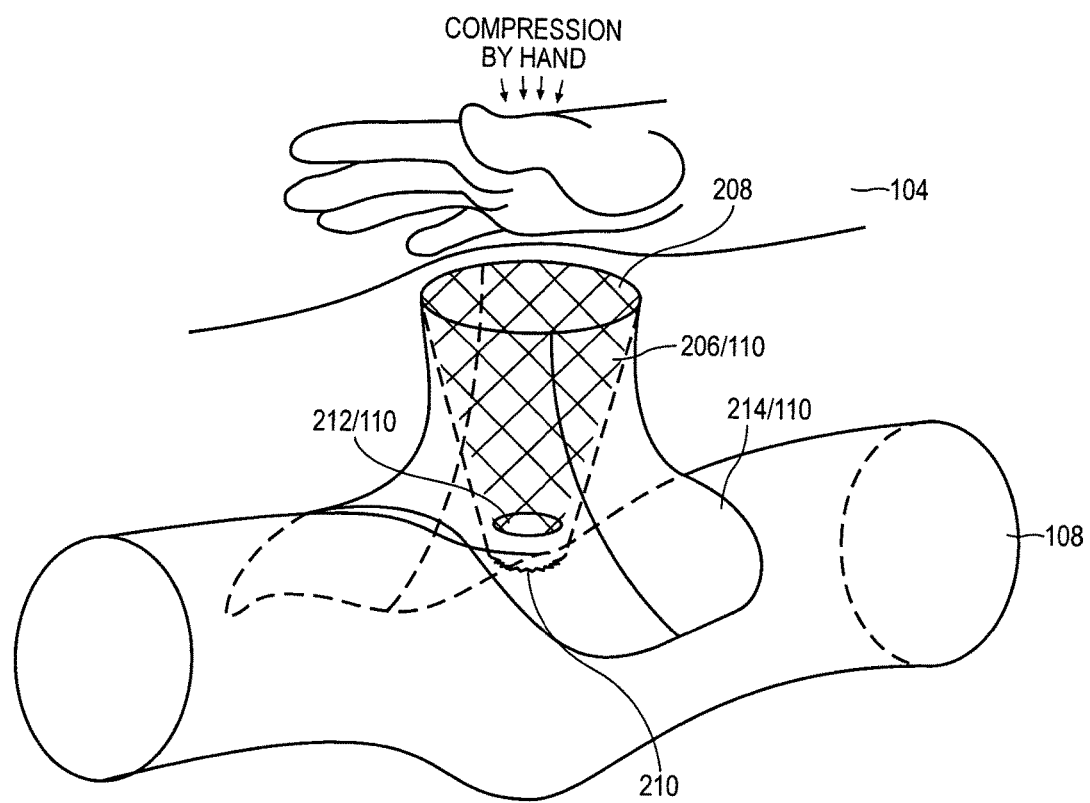
FIG. 7A shows a 3-dimensional view of a further alternative funnel that includes an unidirectional valve at a tapered end of the funnel and a dog-bone liked saddle distal to the tapered end of the funnel in accordance with an embodiment.
Figure 7B:
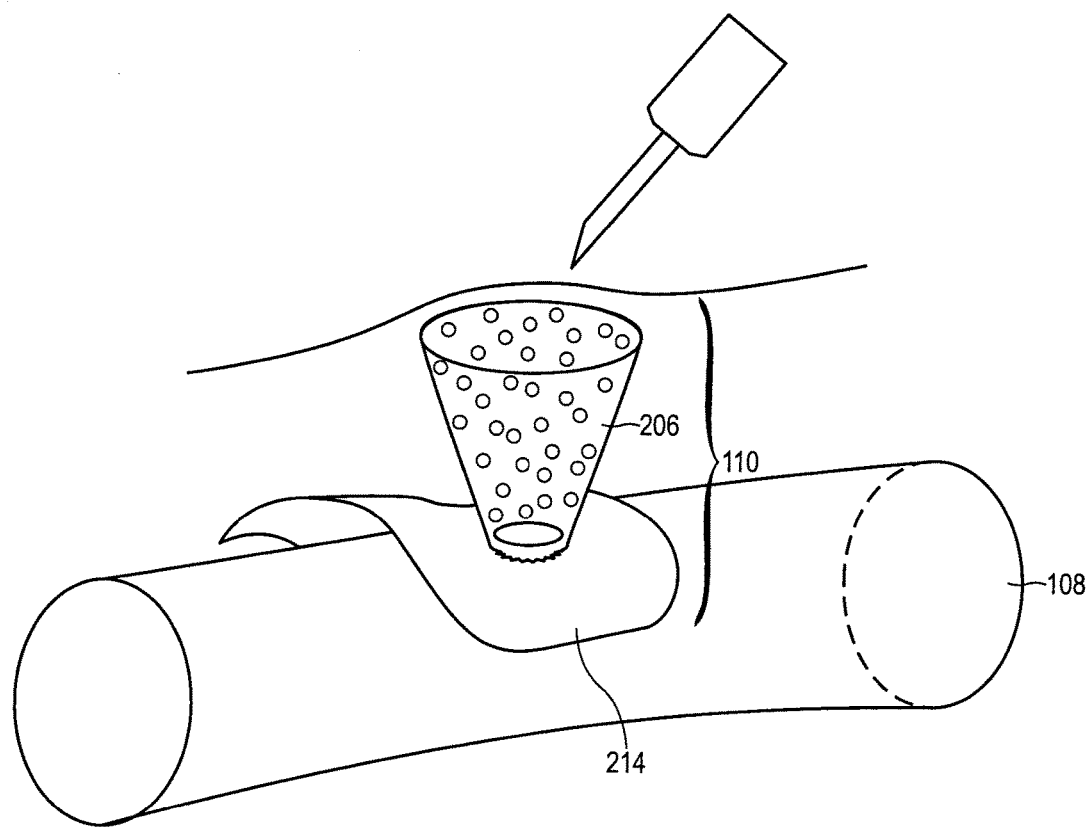
FIG. 7B shows a 3-dimensional view of the further alternative funnel injected with gel with healing or antimicrobial properties and a dog-bone-like saddle that functions to limit the lateral movement of a blood vessel away from the funnel in accordance with an embodiment.

FIG. 7A and FIG. 7B illustrate a further embodiment of the guiding portion 110 that provides further features such as non-invasive vessel anchoring and anti-infection properties.

FIG. 7A shows a 3-dimensional view of a further embodiment of a guiding portion 110 that includes a channel portion or funnel 206 including an inlet 208 and an outlet 210, wherein the channel portion 206 is configured to be resorbed over time. The guiding portion 110 further includes a unidirectional valve 212 positioned adjacent to the outlet 210 of the channel portion 206. The guiding portion 110 also includes an anchor portion 214 positioned adjacent to the outlet 210 of the channel portion 206 and configured to substantially anchor the channel portion 206 onto the blood vessel 108.

In more details, the funnel or channel portion 206 includes the unidirectional valve 212 at a tapered end or the outlet of the funnel 206 and a dog-bone liked saddle or the anchor portion 214 distal to the tapered end of the funnel 206 in accordance with an embodiment. FIG. 7A further includes an option of the funnel or channel portion 206 being configured or injectable with anti-bacteria or anti-microbial gel.

The unidirectional valve 212 at the tapered end of the funnel 206 prevents backflow of the blood into the funnel 206 when the needle (not shown) of the vascular access device (not shown) is withdrawn. Further, the unidirectional valve 212 provides pressure focused at the needled penetrated location of the vessel 108 when compression from the skin layer 104 is applied, resulting in a significantly more effective and focused hemostasis. Applying both stoppage of backflow and focused hemostasis in combination, the funnel or channel portion 206 may eliminate or greatly reduce the build up on scabs outside the blood vessel 108 and within the funnel or channel portion 206. The absence of scabs as a nidus for bacteria, such as staphylococcus, and other microorganisms will significantly reduce the risk of infection for the patient. The unidirectional valve 212 may be constructed with leaflets in the shape of a duckbill and made of elastomeric components, which allows the entry of the needle (not shown) into the blood vessel 108. Upon withdrawal of the needle, the elastomeric lips will purse together to prevent blood in the blood vessel 108 from entering the funnel 206.

FIG. 7B shows a 3-dimensional view of the further alternative of a guiding portion 110 that includes a funnel 206 injected with gel with healing or anti-microbial properties and a dog-bone-like saddle 214 that functions to limit the lateral movement of a blood vessel 108 away from the funnel 206 in accordance with an embodiment.

Injecting the funnel or channel portion 206 with gel, with healing or anti-microbial properties may act as an additional measure against infection. Further, the dog-bone shaped feature 214 may function as a non-invasive saddle to limit the lateral movement of the blood vessel 108 away from the funnel 206. With a curvature radius of about 2 mm to about 5 mm, the saddle 214 may allow the funnel 206 to sit snugly on the blood vessel 108 to improve the needling accuracy for penetration into the blood vessel 108.

Figure 8A:
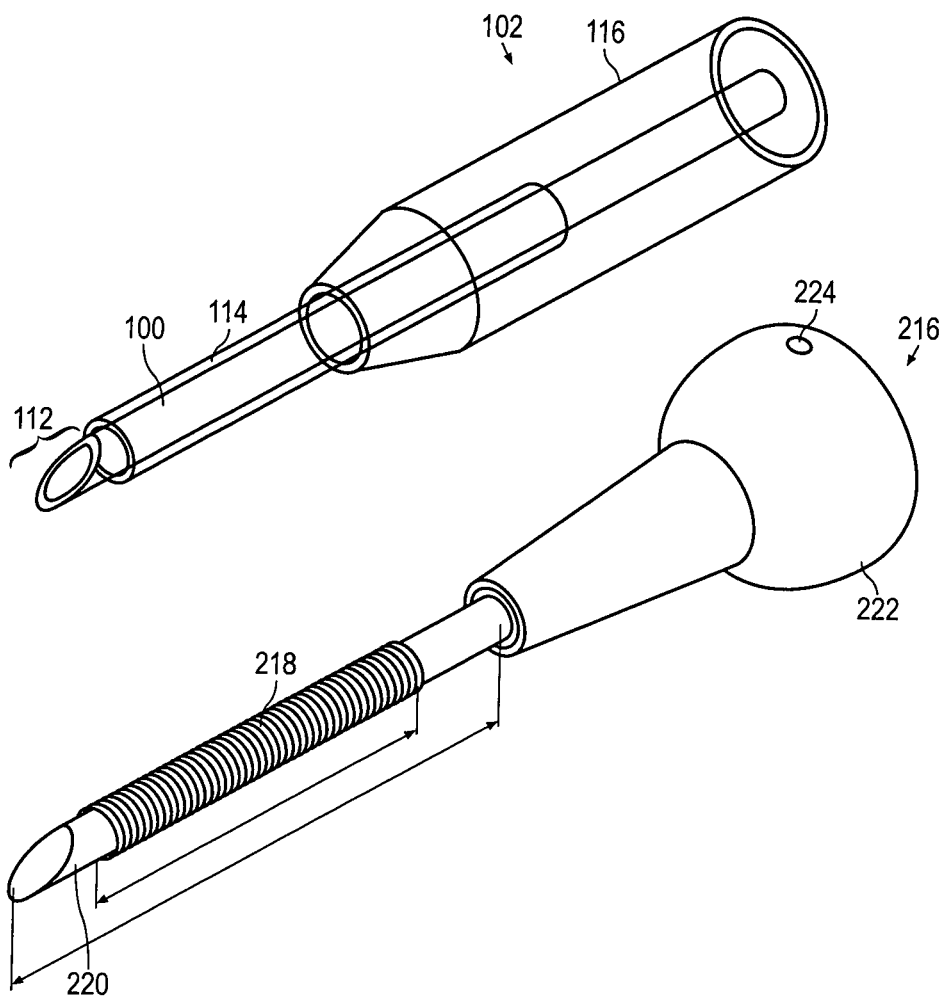
FIG. 8A shows a 3-dimensional view of the vascular access device and a tissue scarring device used for ablation purposes in accordance with an embodiment.

FIGS. 8A to 8F show a further embodiment that removes the need for implantation by inducing a scarred tissue track directly, such as through tissue ablation or tissue removal technologies. To achieve this, a tissue scarring needle or tissue scarring vascular access needle 220 is coupled with an ablation and/or tissue removal electrode 218 as shown in FIG. 8A. Such electrodes 218 may be an ablation coil wounded around the tissue scarring needle 220 that may be inserted together with the tissue scarring needle 220 during the first insertion procedure. Ablation electrodes 218 may adopt different ablation modalities, including but not limited to radiofrequency, high intensity focused ultrasound (HIFU), microwave, cryothermic systems, laser or other modalities as disclosed in the art. For tissue removal, electrodes could adopt modalities as histotripsy and energized saline jets. This system is an alternative embodiment that removes the need for implantation by creating a buttonhole (BH) track (it is the scarred tissue track that is formed) directly through tissue ablation.

FIG. 8A also shows a 3-dimensional view of a vascular access device 102 in addition to the tissue scarring device 216 used for ablation purposes. The vascular access device 102 is similar to that shown in FIG. 1B and FIG. 5A. The vascular access device 102 may include a needle 100 having a tip portion 112; and a shield 114 arranged around and at least substantially along a longitudinal axis (not shown) of the needle 100, wherein the shield 114 is substantially rigid so as to provide strength to the tip portion 112 to penetrate a tissue layer (not shown) as the tip portion 112 extends out from the shield 114 and the needle 100 gradually loses column strength as the distance between the tip portion 112 and the shield 114 increases. The vascular access device 102 may additionally include an actuating portion 116 coupled to a portion of the needle 100. The tissue scarring device 216 may include the tissue scarring needle 220, with the ablation electrode 218 wound around the tissue scarring needle 220. The tissue scarring needle 220 may be coupled to a holder 222 and an indicator 224 may be positioned on the holder 222 to indicate if the tissue scarring device 216 is being activated or not. The length of the tissue scarring needle 220 may be between about 4 mm to about 20 mm while the length of the ablation electrode 218 may be between about 3 mm to about 12 mm. The diameter of the tissue scarring needle 220 may be in the range of 1.270 mm (18 G) to 2.108 mm (14 G). In FIG. 8A, both the vascular access needle 100 and the tissue scarring device 220 are shown. The tissue scarring needle 220 may include a material selected from a group consisting of metals and polymers. The holder 222 may be of the particular shape as shown in FIG. 8A but may also be of any other suitable shapes which allow ease of use and for acceptable grip by the patient.

In all of the previously described embodiments, the funnel, track or channel portion 206 includes a proximal end and a distal end. When the funnel, track or channel portion is implanted, the distal end is positioned above the blood vessel 108 and the proximal end is positioned below the outer skin layer 104. Both the proximal and distal ends are contained entirely between the blood layer and the skin layer in a manner that is non-invasive with respect to the blood vessel.

In FIGS. 8B to 8F, a method to obtain access to a blood vessel 108 underneath a skin layer 104 may be disclosed. The method may include inserting the tissue scarring device 216 through the skin layer 104 to reach the blood vessel 108; and forming a resultant scarred track between the blood vessel 108 and the skin layer 104 as the tissue scarring device 216 is retracted. The tissue scarring device 216 may include an ablation coil 218 or a combination of a tissue scarring needle 220 and the ablation coil 218.

Figure 8B:
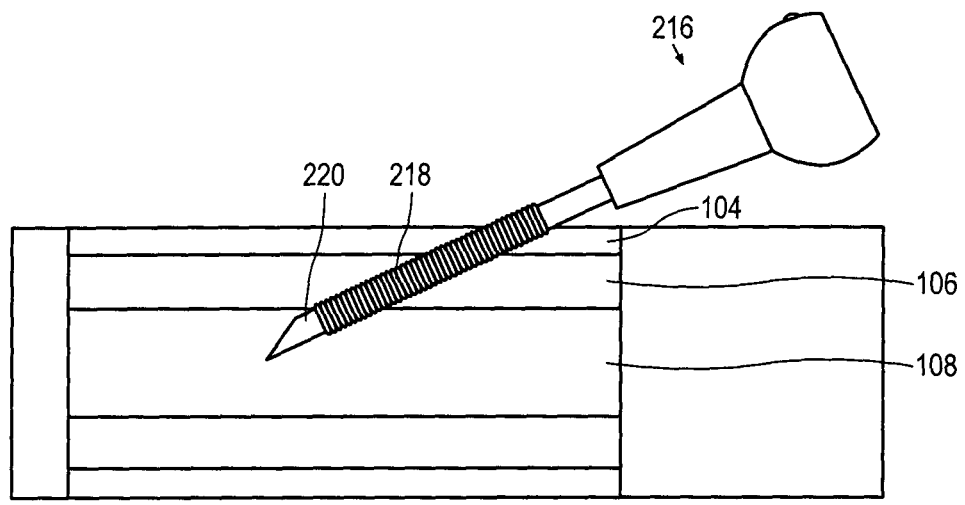
FIG. 8B shows a cross-sectional side view of the tissue scarring device including a tissue scarring needle coupled with an ablation coil being inserted into a vessel in accordance with an embodiment.

FIG. 8B shows a cross-sectional side view of the tissue scarring device 216 including the tissue scarring needle 220 coupled with the ablation coil 218 being inserted into a vessel 108 (when in use) in accordance with an embodiment. In FIG. 8B, the tissue scarring needle 220 coupled with the ablation coil 218 is inserted through the skin layer 104, the subcutaneous tissue layer 106 to the vessel 108 to gain vascular access. The tissue scarring needle 220 may be positioned at any suitable angle depending on the user. However, it would be preferred to positioned the tissue scarring needle 220 at an angle relative to the plane of the skin layer 104 which allows ease of penetration of the tissue scarring needle 220, for example between about 25° to 65°.

Figure 8C:
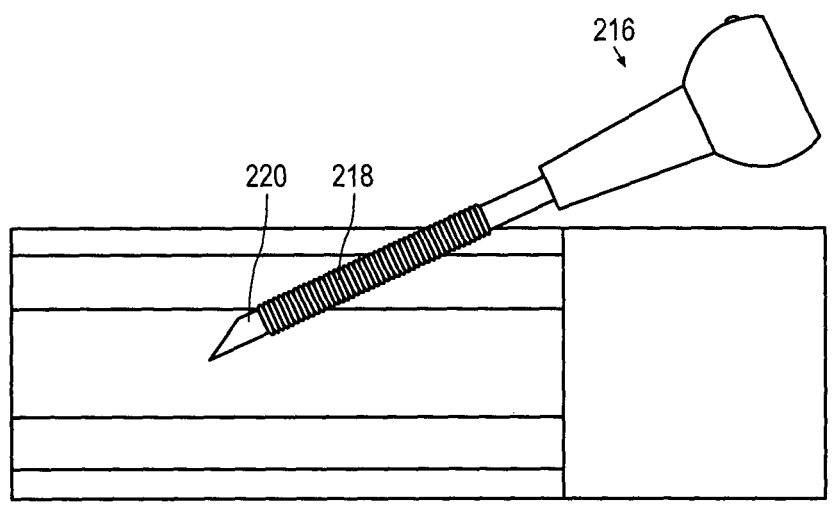
FIG. 8C shows a cross-sectional side view of the ablation coil being activated and thus emitting energy suitable for local ablation of tissue in accordance with an embodiment.

FIG. 8C shows a cross-sectional side view of the ablation coil 218 being activated and thus emitting energy suitable for local ablation of tissue in accordance with an embodiment. In FIG. 8C, after complete insertion of the tissue scarring needle 220, the ablation coil 218 is activated through the means of a switch (not shown) on the coupled hand-held tissue scarring device 216. The ablation coil 218 may be activated for a sufficient amount of time to allow the local ablation of the tissue 106. The tissue scarring device 216 may be preferably held at a fixed position to prevent excessive ablation of the tissue 106 and creating an opening which is sized so as to accommodate the subsequent insertion of the vascular access needle.

Figure 8D:
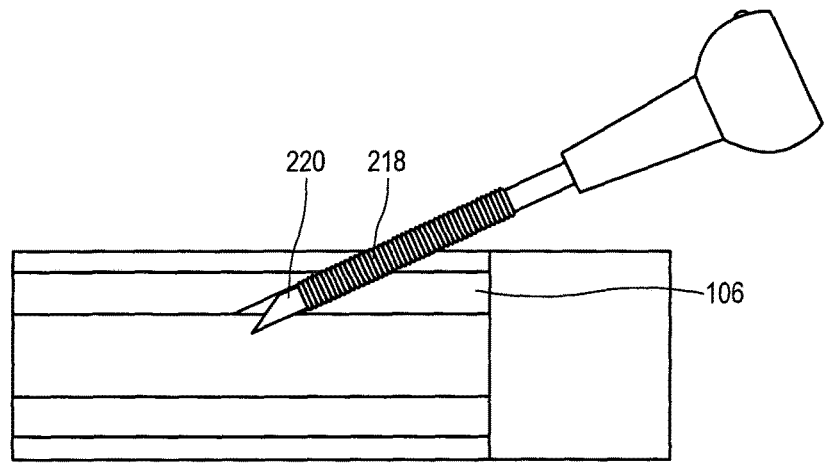
FIG. 8D shows a side cross-sectional view of local ablation of tissue as a result of the emission of the ablation coil in accordance with an embodiment.

FIG. 8D shows a side cross-sectional view of local ablation of tissue 106 as a result of the emission of the ablation coil 218 in accordance with an embodiment. In FIG. 8D, when the ablation coil 218 is activated, the ablation coil 218 emits energy suitable for local ablation of the subcutaneous tissue layer 106. Tissues surrounding the tissue scarring needle 220 that are above the blood vessel are then scarred and form a track that serves as a guide for future needle insertions.

Figure 8E:
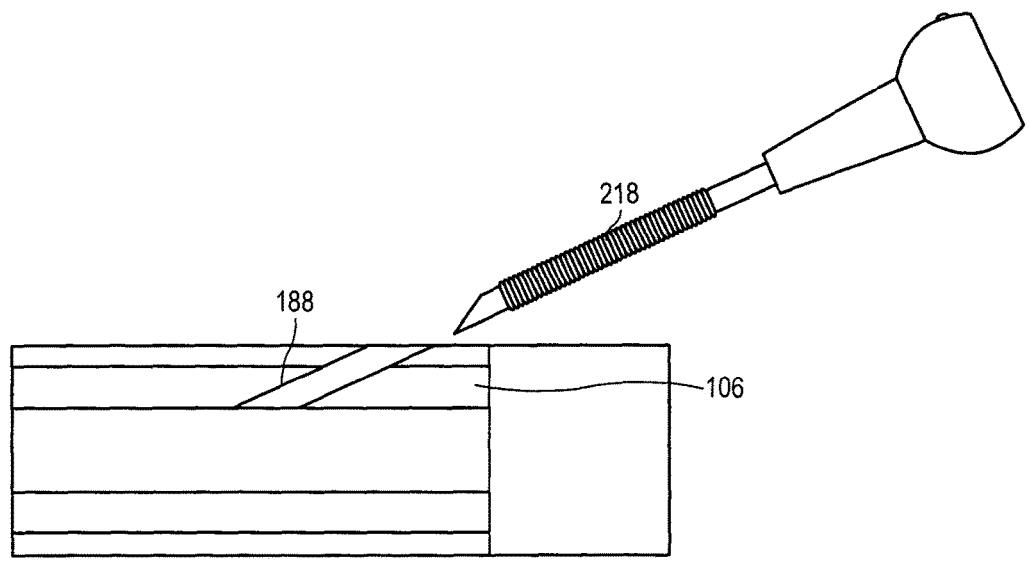
FIG. 8E shows a cross-sectional side view of the ablation coil being deactivated and retracted and a track formed due to local ablation of tissue in accordance with an embodiment.

FIG. 8E shows a cross-sectional side view of the ablation coil 218 being deactivated and retracted and a track 188 formed due to local ablation of tissue in accordance with an embodiment. In FIG. 8E, after the procedure is complete, the tissue scarring needle 220 coupled with the ablation coil 218 is retracted, leaving behind a scarred tissue track 188 in the subcutaneous tissue layer 106.

Figure 8F:
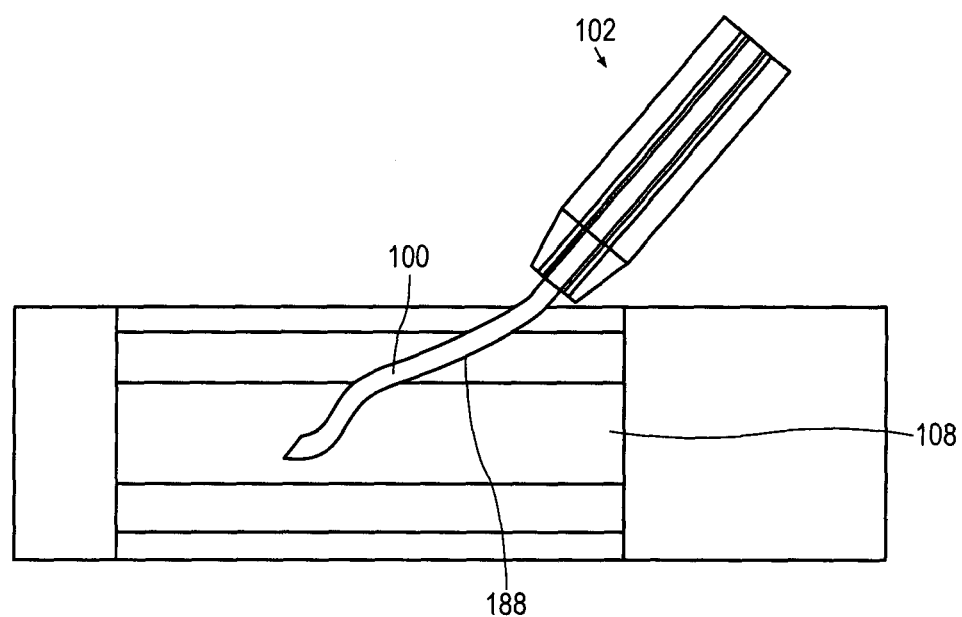
FIG. 8F shows a cross-sectional side view of a needle of a vascular access device without column strength being inserted into the vessel through the track formed by scarred tissue for the purpose of dialysis in accordance with an embodiment.

FIG. 8F shows a cross-sectional side view of a needle 100 of a vascular access device 102 without column strength being inserted into the vessel 108 through the track 188 formed by scarred tissue for the purpose of dialysis in accordance with an embodiment.

In FIG. 8F, the scarred tissue track 188 serves as a guide for the vascular access needle 100 to access the blood vessel 108 through the same path each and every time during dialysis.

In a further embodiment, the modalities of ablation are controlled by the power of a generator, and may be activated by a connected foot pedal. In track formation, positioning of the tissue scarring needle 220 is necessary before ablation. To ensure that the tissue scarring needle 220 as shown earlier in FIGS. 8A to 8E is positioned properly before performing ablation, various safety features may be incorporated to guide or confirm to the user the position.

Upon first insertion of the tissue scarring needle 220, flashback is to be inspected to ensure entry into the vein or blood vessel 108. Flashback may be inspected using an indication chamber in which the user will observe for possible colour change or height indications of flashback, or the tissue scarring device 216 may incorporate a sensor system that determines flashback and provide the user with feedback visually via a display screen or audibly via an audio output. Such a sensor system may make use of electronics, mechanical set-ups, biomolecules, biomarkers, or a combination thereof.

FIG. 8G to FIG. 8L and FIG. 8M to FIG. 8P illustrate embodiments of the tissue scarring device or ablation device 216 customized with safety features specifically for creation of the buttonhole track without causing collateral damage to the target blood vessel.

Figure 8G:
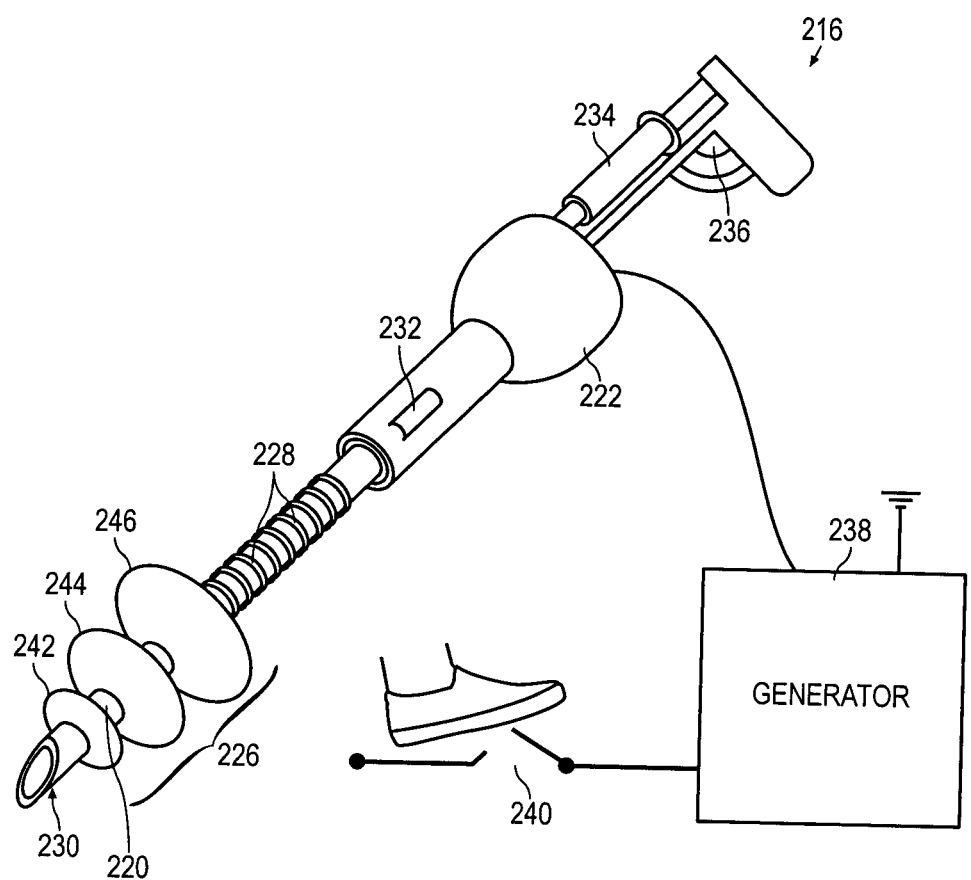
FIG. 8G shows a 3-dimensional perspective view of a tissue scarring device used for ablation purposes with safety features through a serial ballooning system in accordance with an embodiment.
Figure 8H:
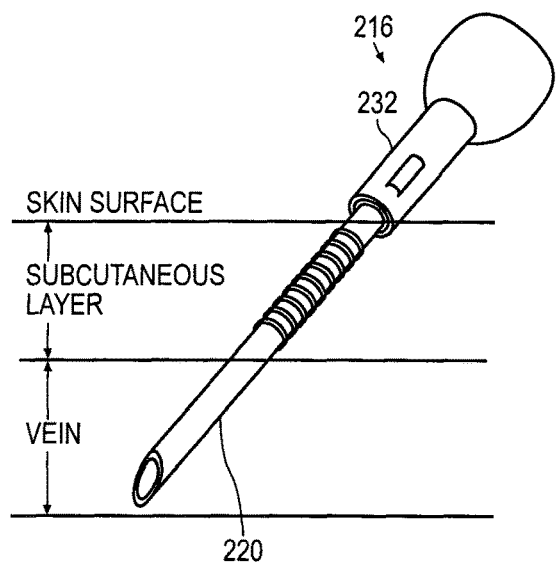
FIG. 8H shows a cross-sectional view of a needle of the tissue scarring device during a first insertion, indicating flashback through a chamber upon vein entry in accordance with an embodiment.

FIG. 8G shows a 3-dimensional perspective view of a tissue scarring device 216 used for ablation purposes with safety features through a serial ballooning system 226 in accordance with an embodiment.

The tissue scarring device 216 includes a tissue scarring needle 220, and electrodes 228 wounded around the tissue scarring needle 220. Further, the serial ballooning system 226 is positioned nearer the tip portion or distal section 230 of the tissue scarring needle 220. The ballooning system 226 includes balloons 242, 244, 246 of varying diameters, with the balloon 242 with the smallest outer diameter positioned nearer to the tip portion 230 of the tissue scarring needle 220 and the balloon 246 with the larger outer diameter positioned furthest from the tip portion 230 of the tissue scarring needle 220. Three balloons 242, 244, 246 may be shown in FIG. 8G, but the number of balloons may vary depending on user and design requirements.

One end of the tissue scarring needle 220 may be adapted for penetrating into the skin layer 104 and the opposite end may be coupled to a hand-held portion or holder 222. A chamber 232 may be positioned on the hand-held portion 222 to observe the flashback. Further, a syringe 234 for balloon inflation may be coupled to the hand-held portion 222 and the syringe 234 may be activated by a trigger 236.

Further, the hand-held portion 222 may be connected to a generator 238 and a foot operated switch 240 may be used to activate the generator 238. However, there may be any other suitable means for activating the generator 238.

Figure 8I:
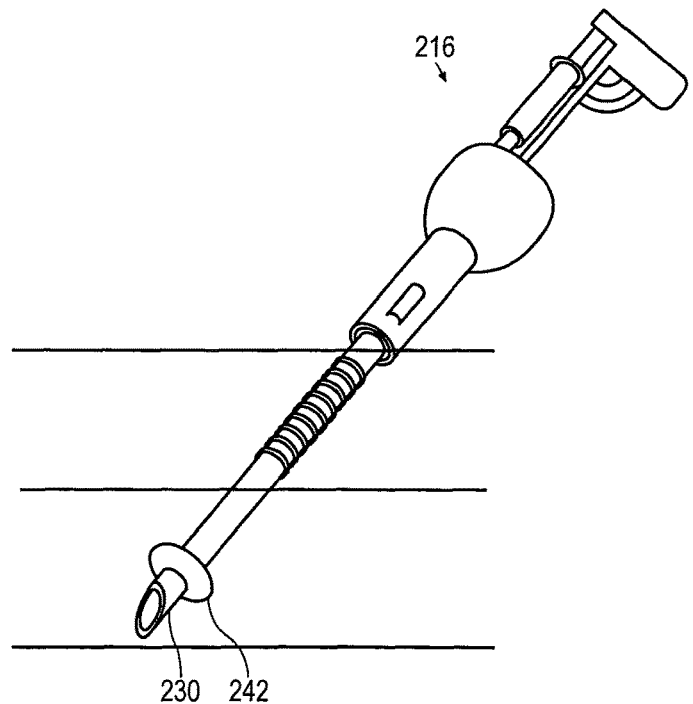
FIG. 8I shows a cross-sectional view of an inflation of a first distal balloon at a needle tip of the tissue scarring device using an inflation system in accordance with an embodiment.
Figure 8J:
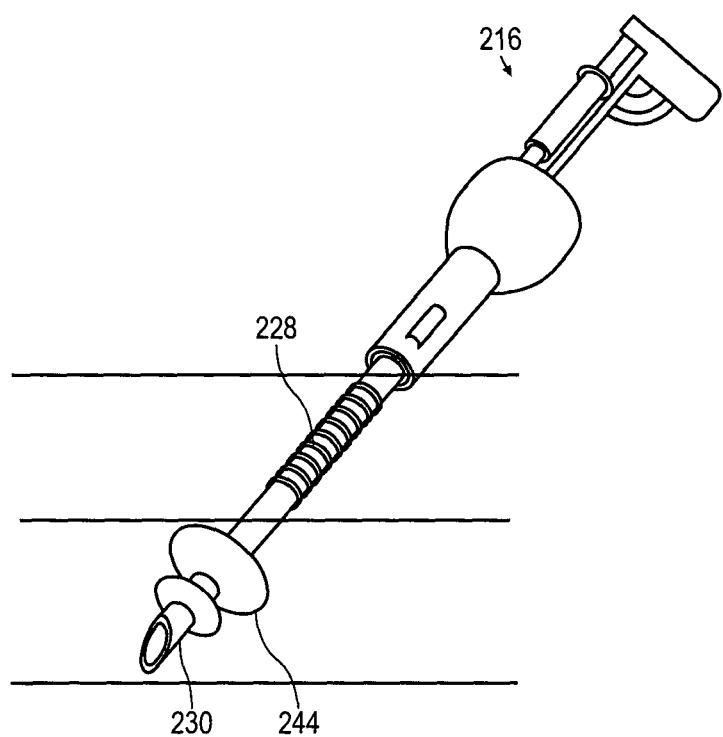
FIG. 8J shows a cross-sectional view of a further inflation of the second distal balloon from the needle tip of the tissue scarring device, the inflation of the second distal balloon is to increase the distance of the electrodes from the vein in accordance with an embodiment.
Figure 8K:
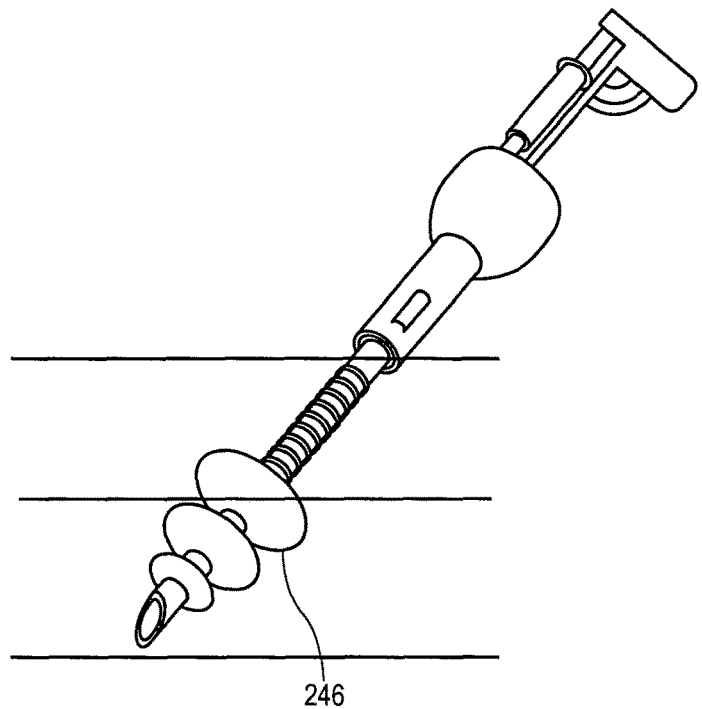
FIG. 8K shows a cross-sectional view of a yet further inflation of the largest balloon and upon successful inflation, the switch is then enabled in accordance with an embodiment.
Figure 8L:
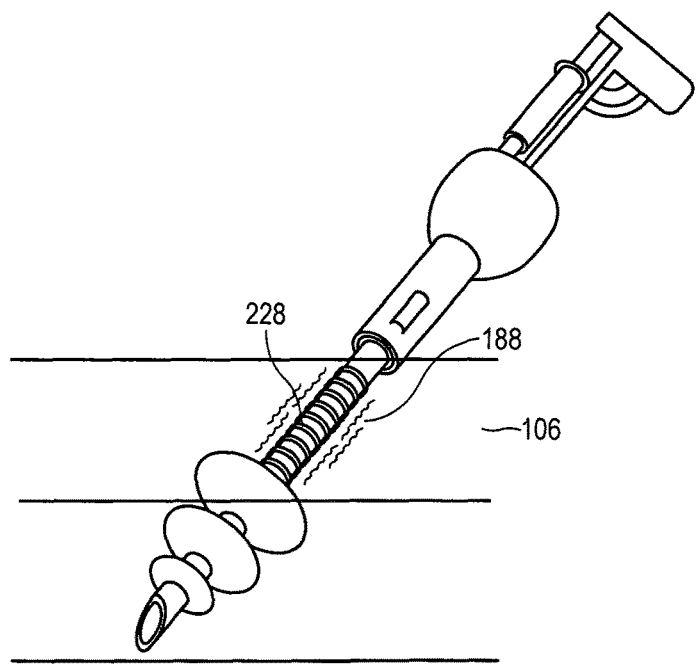
FIG. 8L shows a cross-sectional view of successful activation of ablation coil to emit energy suitable for ablation, hence scarring and forming a scarred tissue track in a subcutaneous layer in accordance with an embodiment.

FIG. 8H to FIG. 8L illustrates use of the serial ballooning system 226 including a trigger 236 and syringe 234 for balloon inflation. In more details, FIG. 9H shows a cross-sectional view of a tissue scarring needle 220 of the tissue scarring device 216 during a first insertion, indicating flashback through the chamber 232 upon vein entry in accordance with an embodiment, FIG. 8I shows a cross-sectional view of an inflation of a first distal balloon 242 at a needle tip 230 of the tissue scarring device 216 using an inflation system in accordance with an embodiment, FIG. 8J shows a cross-sectional view of a further inflation of the second distal balloon 244 from the needle tip 230 of the tissue scarring device 216, the inflation of the second distal balloon 244 is to increase the distance of the electrodes 228 from the vein in accordance with an embodiment, FIG. 8K shows a cross-sectional view of a yet further inflation of the largest balloon or third balloon 246 and upon successful inflation, the foot pedal switch 240 as shown in FIG. 8A is then enabled in accordance with an embodiment, FIG. 8L shows a cross-sectional view of successful activation of the ablation coil or electrodes 228 to emit energy suitable for ablation, hence scarring and forming a resultant scarred tissue track 188 in a subcutaneous layer 106 in accordance with an embodiment;

In this regard, upon inspection of flashback, the balloons 242, 244, 246 of increasing diameters, consecutively placed along the needle tip 230, are inflated in the sequence from the distal end of the needle 220 to the proximal ablation electrodes 228. This may be a means to create a safe distance from the vessel wall. Upon successful ballooning, ablation electrodes 228 may be activated upon the stepping of the foot pedal switch 240 which may be coupled to the generator 238.

FIGS. 8M to 8P illustrate the second embodiment where the system may use impedance detectors 196 between the electrodes 228. This alternative embodiment utilizes an impedance sensor in a closed-loop system coupled with the ablation electrodes 228.

Figure 8M:
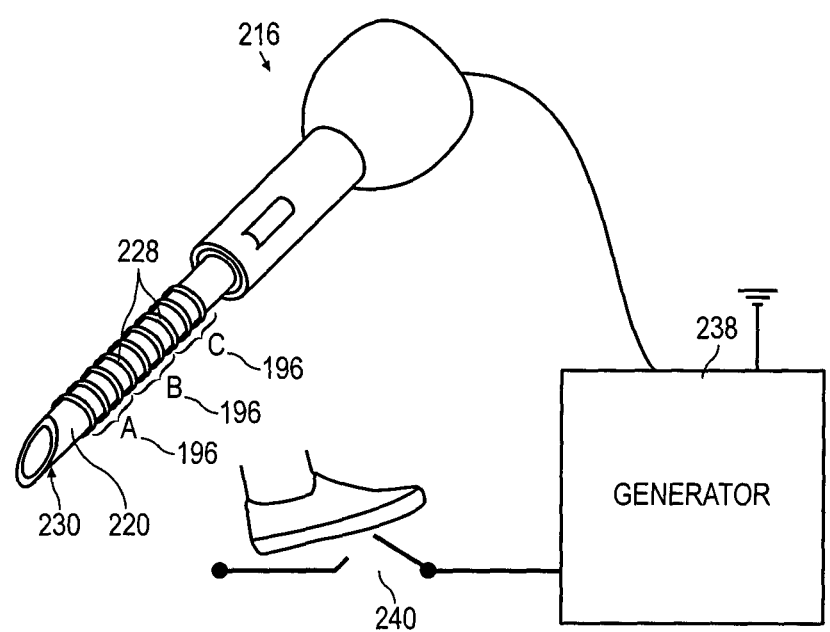
FIG. 8M shows a cross-sectional view of a tissue scarring device for ablation purposes with safety features through an impedance detection method in accordance with an embodiment.

FIG. 8M shows a cross-sectional view of a tissue scarring device 216 for ablation purposes with safety features through an impedance detection method in accordance with an embodiment. In FIG. 8M, different segments A, B and C between the electrodes 228 may represent the impedance detectors 196. Segment A is positioned nearest to the tip portion of the tissue scarring needle 220, followed by segment B and then segment C being furthest away from the tip portion 230 of the tissue scarring needle 220. Impedance detection at the coil of electrodes 228 proximal to the tip portion 230 of the tissue scarring needle 220 may be executed. Depending on extent of entry of the tissue scarring needle 220 into the vessel (not shown), each electrode band (segment A, B or C) will be surrounded by either tissue or blood, and will hence register different voltage/current output since resistivity of tissue and blood is different. These values are calculated by a back-end architecture that includes a generator 238 and a processor (not shown).

Based on detection of differential resistivity of blood ($\rho$=65-150 $\Omega$cm) and tissue samples ($\rho$=200-5,000 $\Omega$cm), blood impedance detectors 196 sensing the location of electrodes outside the bloodstream will actuate the activation of a particular segment of electrodes 228. The blood impedance detectors 196 are housed in electrode bands (segment A, B or C) along the shaft of the tissue scarring needle 220 and can detect difference in resistivity (depending on contact with either tissue or blood) via voltage/current outputs.

For segments detected to be within the bloodstream, the electrodes 228 in a defined vicinity of that segment cannot be activated despite the activation of the generator 238 by a foot operated switch 240.

Figure 8N:
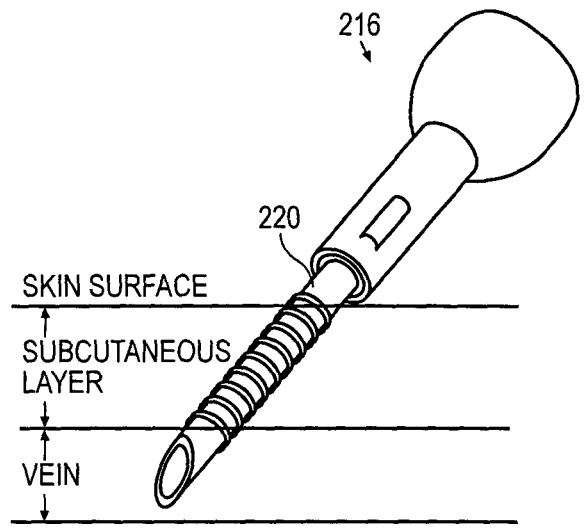
FIG. 8N shows a cross-sectional view of a needle of a tissue scarring device during a first insertion, indicating flashback upon blood vessel entry in accordance with an embodiment.
Figure 8O:
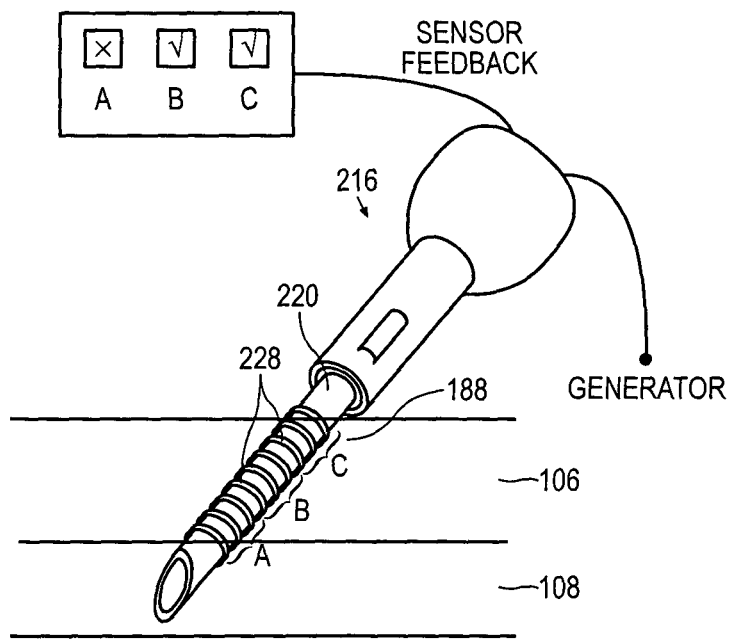
FIG. 8O shows a cross-sectional view of a needle of a tissue scarring device where only segment A of the ablation electrodes has entered the blood vessel, but not segments B or C in accordance with an embodiment.
Figure 8P:
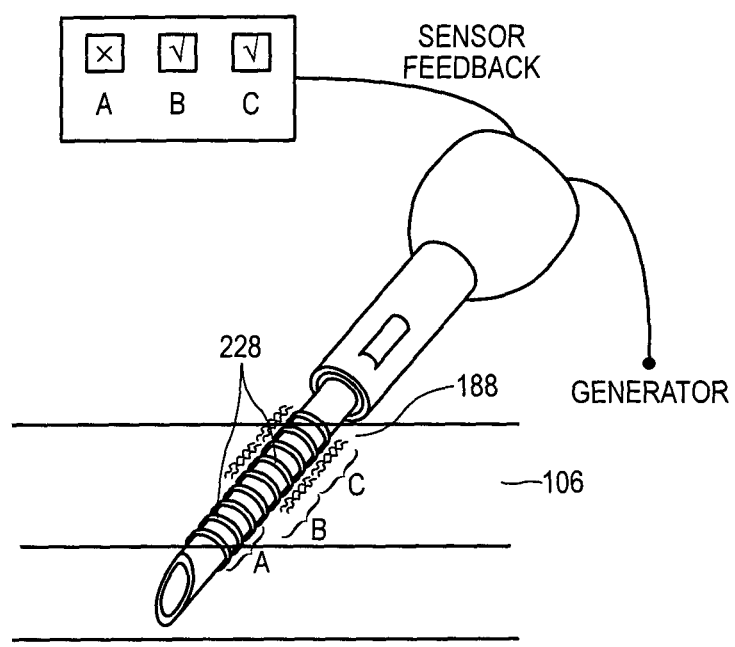
FIG. 8P shows a cross-sectional view of successful activation of the ablation coil in segments B and C only to emit energy suitable for ablation, hence scarring and forming a scarred tissue track in the subcutaneous layer in accordance with an embodiment.

FIG. 8N shows a cross-sectional view of the tissue scarring needle 220 of a the tissue scarring device 216 during a first insertion, indicating flashback upon blood vessel entry in accordance with an embodiment, FIG. 8O shows a cross-sectional view of the tissue scarring needle 220 of a tissue scarring device 216 where only segment A of the ablation electrodes 228 has entered the blood vessel 108, but not segments B or C in accordance with an embodiment, FIG. 8P shows a cross-sectional view of successful activation of the ablation coil 228 in segments B and C only to emit energy suitable for ablation, hence scarring and forming a scarred tissue track 188 in the subcutaneous layer 106 in accordance with an embodiment.

Figure 9:
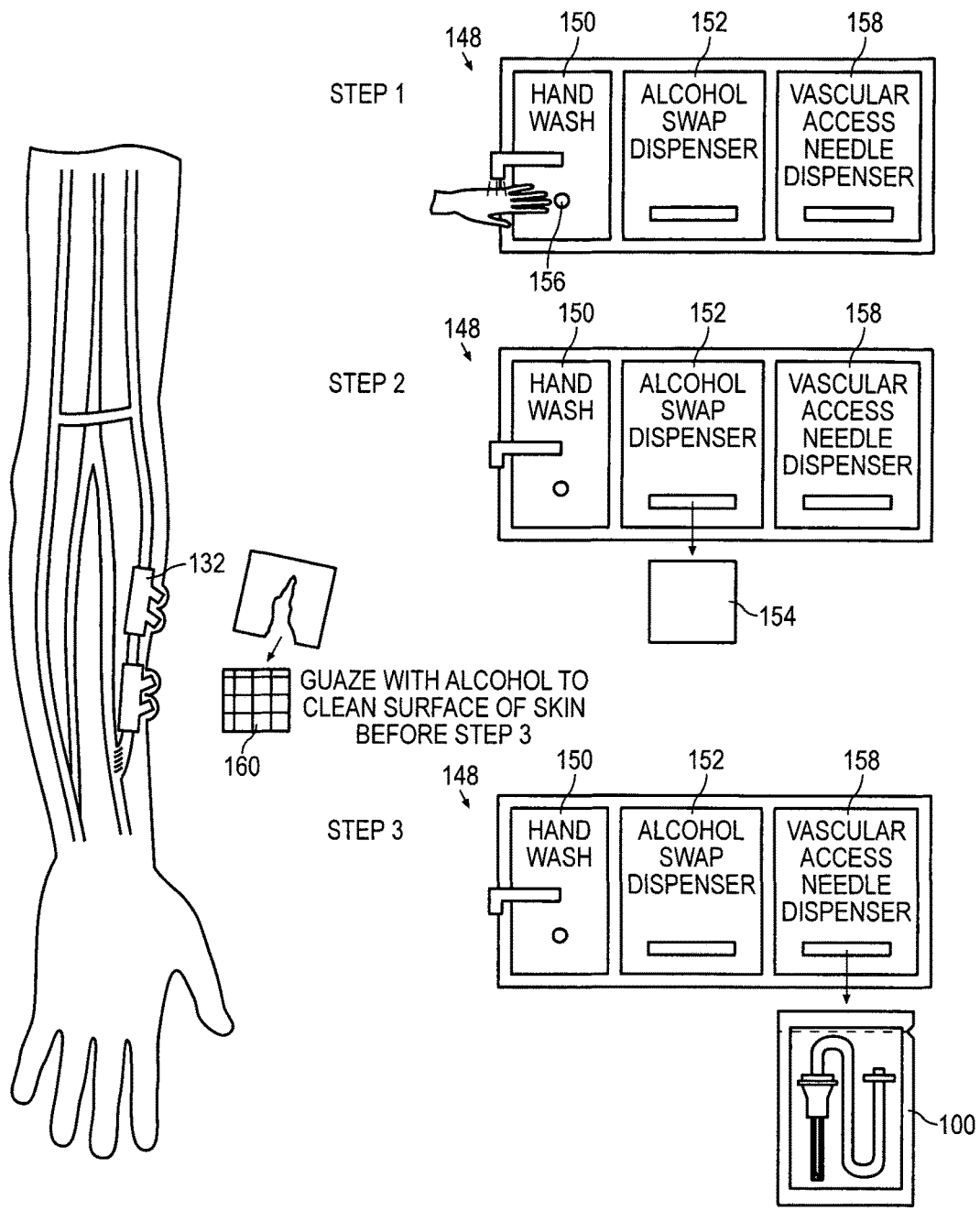
FIG. 9 shows a side view of a backend vascular access needle dispenser that ensures patient performs hand hygiene, follow by skin disinfection before proceeding with needling using a vascular access needle and a cuff system in accordance with an embodiment.

FIG. 9 shows a side view of a backend vascular access needle dispenser system 148 that ensures patient performs hand hygiene, follow by skin disinfection before proceeding with needling using a vascular access needle 100 as shown in FIG. 1B and a cuff system 132 as shown in FIG. 3A in accordance with an embodiment.

FIG. 9 illustrates how the vascular access needle dispenser system 148 works and how the needle dispenser 158 mandates users to comply with hand wash and surface disinfection protocols before the vascular access needle 100 can be dispensed. To begin, in step 1, the patient must wash his/her hands with the sanitizer dispensed from the hand wash compartment 150, before an alcohol swab 154 can be dispensed from the alcohol swab dispenser 152 in step 2. The hand wash compartment 150 may have a sensor 156 for sensing the presence of a body, e.g. hand, so that sanitizer may be dispensed. The alcohol swab 154 including a gauze 160 with alcohol wrapped within is expected to be used to sanitize the skin where the vascular access needle 100 will puncture. Only by tapping the sensor (not shown) on the alcohol swab wrapper 154 onto the vascular access needle dispenser 158, can the vascular access dispenser 158 dispense the vascular access needle 100 in step 3. By mandating the user washes he/her hands, cleans the puncture site, before the vascular access needle 100 can be dispensed, the vascular access needle dispenser system 148 ensures that this patient-operated procedure is performed with little or no chance of infection due to non-compliance of hygiene protocol.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

The invention claimed is:

1. A method of obtaining access to a blood vessel underneath a skin layer, the method comprising:
    providing a guiding portion and placing said guiding portion beneath the skin layer and above the blood vessel to receive and guide a needle to reach the blood vessel, the guiding portion comprising a channel portion comprising an inlet and an outlet;

accessing the blood vessel with a vascular access device comprising:
a needle having a tip portion; and
a rigid sheath axially translatable with respect to the tip portion arranged around and at least substantially along a longitudinal axis of the needle;
wherein the tip portion penetrates a tissue layer overlying the guiding portion, and the rigid sheath provides strength for said penetration as the tip portion extends out from the rigid sheath;
wherein the needle is received by the channel portion inlet, and conforms to the channel portion as the distance between the tip portion and the rigid sheath increases; and
wherein the outlet comprises a constriction which causes the needle to regain push force to penetrate the blood vessel.

2. The method according to claim 1,
wherein the vascular access device comprises an actuating portion coupled to a portion of the needle.

3. The method according to claim 2,
wherein the rigid sheath is slidable relative to the tip portion.

4. The method according to claim 2,
wherein the needle extends out from the rigid sheath as the rigid sheath retracts into the actuating portion.

5. The method according to claim 1,
wherein the rigid sheath comprises a sealing portion arranged adjacent to the tip portion so as to seal the needle within the rigid sheath.

6. The method according to claim 1,
wherein the needle further comprises a flexible portion, the flexible portion coupled to the tip portion.

7. The method according to claim 6,
wherein the flexible portion comprises a same material or a different material from the tip portion.

8. The method according to claim 1,
wherein the needle comprises a single material or a combination of materials with varying flexibility.

9. The method according to claim 1,
wherein the channel portion is biodegradable.

10. The method according to claim 1,
wherein the channel portion comprises a porous sidewall with a plurality of holes.

11. The method according to claim 1,
wherein the channel portion comprises at least one helical screw.

12. The method according to claim 1,
wherein the channel portion comprises a frusto-conical portion.

13. The method according to claim 1,
wherein the channel portion further comprises a tubular portion.

14. The method according to claim 1,
wherein the guiding portion further comprises an unidirectional valve positioned adjacent to the outlet of the channel portion.

15. The method according to claim 1,
wherein the guiding portion further comprises an anchor portion positioned adjacent to the outlet of the channel portion and to noninvasively anchor the channel portion over the blood vessel.

16. The method according to claim 15,
wherein the anchor portion comprises a dog-bone shaped portion.

17. The method according to claim 1,
wherein the channel portion is configured to be filled with an anti-bacteria or anti-microbial gel.

18. The method according to claim 1,
wherein the channel portion is positioned at an angle relative to a plane of the skin layer.

19. The method according to claim 1,
wherein the guiding portion is resorbed over time, thereby forming a scarred tissue track configured to serve as a guide for subsequent access of the vascular access device.

20. The method according to claim 1,
wherein the needle is configured to conform to an orientation of the blood vessel after penetration of the blood vessel.

* * * * *